US011160893B2

(12) United States Patent
Grossman et al.

(10) Patent No.: US 11,160,893 B2
(45) Date of Patent: Nov. 2, 2021

(54) INFECTION CONTROL METHOD AND SYSTEM

(71) Applicant: Allied Bioscience, Inc., Plano, TX (US)

(72) Inventors: Craig Grossman, Point Roberts, WA (US); Ingrida Grossman, Point Roberts, WA (US); Gavri Grossman, Point Roberts, WA (US)

(73) Assignee: Allied Bioscience, Inc., Plano, TX (US)

( * ) Notice: Subject to any disclaimer, the term of this patent is extended or adjusted under 35 U.S.C. 154(b) by 505 days.

(21) Appl. No.: 16/013,127

(22) Filed: Jun. 20, 2018

(65) Prior Publication Data
US 2018/0369437 A1 Dec. 27, 2018

Related U.S. Application Data

(60) Provisional application No. 62/524,320, filed on Jun. 23, 2017, provisional application No. 62/524,313, filed on Jun. 23, 2017.

(51) Int. Cl.
A61L 2/24 (2006.01)
C12Q 1/06 (2006.01)
(Continued)

(52) U.S. Cl.
CPC ............................ A61L 2/24 (2013.01);
A61L 2/18 (2013.01); A61L 2/22 (2013.01);
C12Q 1/04 (2013.01);
(Continued)

(58) Field of Classification Search
CPC ..... A61L 2/24; A61L 2/22; A61L 2/18; A61L 2202/15; A61L 2202/16; A61L 2202/25;
(Continued)

(56) References Cited

U.S. PATENT DOCUMENTS 6,017,561 A 1/2000 Zhou et al.
6,080,387 A 6/2000 Zhou et al.
(Continued)

FOREIGN PATENT DOCUMENTS

WO 2014049370 4/2014
WO 2014089559 6/2014
(Continued)

OTHER PUBLICATIONS

International Report on Patentability dated May 15, 2019 in PCT/US2018/038474.
(Continued)

Primary Examiner — Regina M Yoo
(74) Attorney, Agent, or Firm — Snell & Wilmer L.L.P.

(57) ABSTRACT

A method for controlling infections in a facility such as a hospital or foodservice establishment is provided. The method comprises tagging assets, monitoring asset location and pathogen contamination for each asset over time, analyzing data sets to identify which assets are the critical control points for pathogen transfer, and coating a residual self-sanitizing coating composition on each asset identified as a critical control point. The infection control method shuts down pathogen transfer routes by mitigating or eliminating pathogen growth on the critical control points.

15 Claims, 5 Drawing Sheets

(51) Int. Cl.
    *C12Q 1/6869*     (2018.01)
    *A61L 2/18*     (2006.01)
    *G06K 19/06*     (2006.01)
    *G06K 7/10*     (2006.01)
    *G06K 7/14*     (2006.01)
    *G06K 19/077*     (2006.01)
    *A61L 2/22*     (2006.01)
    *C12Q 1/04*     (2006.01)
    *C12Q 1/6888*     (2018.01)

(52) U.S. Cl.
    CPC ............ *C12Q 1/06* (2013.01); *C12Q 1/6869* (2013.01); *C12Q 1/6888* (2013.01); *G06K 7/10475* (2013.01); *G06K 7/1413* (2013.01); *G06K 19/06028* (2013.01); *G06K 19/07758* (2013.01); *A61L 2202/14* (2013.01); *A61L 2202/15* (2013.01); *A61L 2202/16* (2013.01); *A61L 2202/25* (2013.01)

(58) Field of Classification Search
    CPC ..... A61L 2202/14; C12Q 1/04; C12Q 1/6888; C12Q 1/06; C12Q 1/6869; G06K 19/06028; G06K 7/10475; G06K 7/1413; G06K 19/07758
    See application file for complete search history.

(56) References Cited

U.S. PATENT DOCUMENTS

| | | |
|---|---|---|
| 6,270,754 B1 | 8/2001 | Zhou et al. |
| 6,482,392 B1 | 11/2002 | Zhou et al. |
| 9,107,973 B1 | 8/2015 | Robinson et al. |
| 9,528,009 B2 | 12/2016 | Grossman et al. |
| 9,757,769 B2 | 9/2017 | Grossman et al. |
| 9,855,584 B2 | 1/2018 | Grossman et al. |
| 9,856,360 B2 | 1/2018 | Moros et al. |
| 9,918,475 B2 | 3/2018 | Moros et al. |
| 9,963,596 B2 | 5/2018 | Moros et al. |
| 10,668,180 B2 * | 6/2020 | Thompson ............. G16H 40/40 |
| 2008/0102485 A1 * | 5/2008 | Dodd ...................... C12Q 1/04 435/34 |
| 2009/0275075 A1 * | 11/2009 | Dodd ...................... C12Q 1/22 435/34 |
| 2010/0008921 A1 | 1/2010 | Pohlner et al. |
| 2012/0291667 A1 | 11/2012 | Geoffrion et al. |
| 2014/0167917 A2 | 6/2014 | Wallace et al. |
| 2015/0118017 A1 | 4/2015 | Yato |
| 2015/0165459 A1 | 6/2015 | Venard et al. |
| 2015/0205985 A1 | 7/2015 | Jinadatha |
| 2015/0314026 A1 | 11/2015 | Mauzerall et al. |
| 2016/0171179 A1 | 6/2016 | Donofrio et al. |
| 2016/0306934 A1 * | 10/2016 | Sperry .................... G06F 3/147 |
| 2017/0081707 A1 | 3/2017 | Dillon et al. |

FOREIGN PATENT DOCUMENTS

| | | |
|---|---|---|
| WO | 2016073634 | 5/2016 |
| WO | 2016130837 | 8/2016 |

OTHER PUBLICATIONS

International Report on Patentability dated May 15, 2019 in PCT/US2018/038463.
Non-Final Office Action dated May 9, 2019 in U.S. Appl. No. 16/013,185.
International Search Report and Written Opinion dated Sep. 17, 2018 in PCT/US2018/038463.
International Search Report and Written Opinion dated Aug. 28, 2018 in PCT/US2018/038474.
U.S. Appl. No. 15/938,417, filed Mar. 28, 2018.
U.S. Appl. No. 15/969,576, filed May 2, 2018.

* cited by examiner

| Summary of the Microbial Burden at Medical Center #1 | BASELINE Bacteria CFU/Sample | FOLLOW-UP 4 weeks POST Treatment CFU/Sample | FOLLOW-UP 11 weeks POST Treatment #1 Bacteria CFU/Sample | FOLLOW-UP 11 weeks POST Treatment #2 Bacteria CFU/Sample | FOLLOW-UP 19 weeks POST Treatment #3 Bacteria CFU/Sample |
|---|---|---|---|---|---|
| Total Samples Taken | 114 | 109 | 114 | 110 | 106 |
| Total Positive Samples | 113 | 107 | 110 | 109 | 102 |
| Total Positive COATED Samples | Below the limit of detection | | | | |
| Samples less than 100 cfu/sample | 6 | 30 | 37 | 26 | 20 |
| Samples b/w 100 and 500 cfu/sample | 31 | 44 | 43 | 47 | 43 |
| Samples b/w 500 and 1,000 cfu/sample | 15 | 8 | 14 | 15 | 10 |
| Samples b/w 1,000 and 10,000 cfu/sample | 42 | 17 | 18 | 17 | 30 |
| Samples b/w 10,000 and 100,000 cfu/sample | 14 | 8 | 1 | 5 | 2 |
| Samples greater than 100,000 cfu/sample | 6 | 2 | 1 | 0 | 1 |
| Max Value | 5.00E+05 | 5.00E+05 | 1.48E+05 | 6.60E+04 | 5.00E+05 |
| Minimum Value | 5.00E+00 | 1.00E+01 | 1.00E+01 | 1.00E+00 | 2.00E+00 |
| Average | 2.47E+04 | 1.25E+04 | 2.73E+03 | 1.92E+03 | 6.15E+03 |
| Geometric Mean | 1.48E+03 | 3.32E+02 | 2.07E+02 | 2.97E+02 | 3.63E+02 |
| Percent Reduction of Bacteria to Baseline (Utilizing Geometric Mean) | | 77.56% | 86.02% | 79.96% | 75.50% |

FIG. 5

INFECTION CONTROL METHOD AND SYSTEM

CROSS-REFERENCE TO RELATED APPLICATIONS

This application claims priority to, and the benefit of U.S. Provisional Patent Application Ser. No. 62/524,313, filed Jun. 23, 2017, entitled INFECTION CONTROL METHOD, and U.S. Provisional Patent Application Ser. No. 62/524,320, filed Jun. 23, 2017, entitled INFECTION CONTROL APPARATUS, the disclosures of which are incorporated herein by reference in their entireties for all purposes.

FIELD

The disclosure generally relates to a method and system of infection control, and in particular, to a method that includes identifying critical control points in facilities and spraying those critical control points with a residual self-sanitizing coating to control the spread of infection.

BACKGROUND

Nosocomial infections, "hospital acquired infections" and/or "healthcare associated infections," (collectively HAIs), are infections that otherwise uninfected patients sometimes acquire when receiving medical treatment in a healthcare facility. The U.S. Centers for Disease Control (CDC) estimates that HAIs account for about 1.7 million infections and 99,000 related deaths per year.

The cause of HAIs is often cross-contamination in the hospital. For example, when an improperly sterilized medical device (e.g., an endoscope) or improperly disinfected equipment (e.g., bedrails or x-ray machines) remain contaminated with pathogens and then are placed in contact with an otherwise uninfected patient. Although causation may be obvious, mitigating the problem is often not so simple. Without knowing the specific equipment that was contaminated, countless pieces of equipment would need to be randomly and almost continuously cleaned and sanitized. Such a cleaning effort would take enormous resources, leaving even less time for actual medical procedures. Further, even surfaces identified as presently contaminated may be contaminated again just moments after cleaning and sanitizing the surfaces, resulting in the whole process being futile.

The foodservice industry also has its share of disease, such as in the form of food borne illness. One program exists to identify where in a food service establishment the likely sources of contamination exist. The program is referred to as HACCP (Hazard Analysis and Critical Control Points) and is a systematic preventative approach to food safety. However, the program, although diligent and structured, merely identifies the obvious ways to control pathogens, namely employee hand washing and the rigorous separation between uncooked and cooked foods before, during and after preparation.

In spite of the recent diligence to reduce the HAIs problem in the healthcare profession, and the existence of the HACCP preventative approach to pathogen control in the foodservice industry, what is still needed in both healthcare and foodservice is a system and method for identifying where pathogens reside in a facility at any given time. Moreover, a need exists to know which surfaces are the critical transfer points based on actual pathogen presence and transfer routes. Further, the need still exists for improved methods for coating such contaminated surfaces once identified such that pathogen transfer over time is eliminated entirely.

SUMMARY

In various embodiments, a method of infection control in a facility is provided. In various embodiments, the method results in a decrease in healthcare acquired infections (HAIs) in hospitals and other healthcare facilities by identifying which assets are the critical control points for pathogen transfer and treating those assets with a residual self-sanitizing coating composition.

In general, methods of infection control herein are used to identify and treat pathogen transfer points in facilities. More specifically, the method enables (a) detection and identification of pathogens on various stationary or movable assets within a facility, (b) tracking asset and pathogen movement around the facility, (c) determination as to which asset surfaces are critical control points based on pathogen counts, genetic mutations and/or pathogen movement routes over time, and (d) coating of those surfaces with a residual self-sanitizing composition that inhibits proliferation of the organisms to pathogenic levels on the surface. In this way, the present method of infection control shuts down pathogen transfer routes by ensuring no pathogens, or only a minimal number of pathogens, can live on the critical control surfaces to be transferred on to other assets and to persons where they may cause infection. In various embodiments, treatment of assets classified as critical control points in a facility keeps the levels of organisms on those assets from reaching pathogenic transfer levels between routine cleaning of the assets. The method eliminates the need to randomly treat all surfaces of all assets in a facility in order to mitigate the spread of infection.

In various embodiments, an infection control method is disclosed. The infection control method may be used in a facility such as a hospital, other healthcare facility or a food service facility. The infection control method may be performed by a computer-based system further comprising an infection control apparatus. The infection control method comprises: (1) creating, by a computer-based system, an asset record for each of one or more assets within a facility; (2) tagging, by the computer-based system, each asset with a barcode or RFID tag associated with each asset record; (3) obtaining, by the computer-based system, a first location for each asset; (4) obtaining, by the computer-based system, a first measure of pathogen contamination for each asset; (5) acquiring, by the computer-based system, the first location and a first measure of pathogen contamination for each asset as a first set of data; (6) obtaining, by the computer-based system, a second location for each asset after passage of a prescribed length of time; (7) obtaining, by the computer-based system, a second measure of pathogen contamination for each asset after passage of the prescribed length of time; (8) acquiring, by the computer-based system, the second location and second measure of pathogen contamination for each asset as a second set of data; (9) analyzing, by the computer-based system, the sets of data to generate a report including a list of assets identified as critical control points; and (10) disposing, by the computer-based system, a residual self-sanitizing coating composition on each asset identified as a critical control point. The lengths of time may be minutes, hours, days, weeks, or months, and may be for example 24 hour prescribed lengths of time.

In various embodiments, steps (6) through (8) may be repeated as many times as necessary to provide additional sets of data for the analyzing step (9).

In various embodiments, the obtaining, by the computer-based system, a second location for each asset after passage of a prescribed length of time further comprises RFID tag inventory by a plurality of RFID readers distributed around the inside of the facility. This automated asset inventory in real time can be initiated by instruction from the computer-based system.

In various embodiments, at least one of obtaining, by the computer-based system, a first measure of pathogen contamination for each asset and obtaining, by the computer-based system, a second measure of pathogen contamination for each asset after passage of the prescribed length of time further comprises swabbing a surface of an asset with an environmental test swab and counting CFU's on inoculated and incubated agar plates.

In various embodiments, the analyzing, by the computer-based system, the sets of data to generate a report including a list of assets identified as critical control points further comprises classifying an asset as a critical control point if the asset meets a predetermined criterion. The predetermined criterion may comprise a measurable pathogen contamination on the asset in two consecutive sets of data, implying that the asset wasn't cleaned properly and may never be cleaned. In various aspects, the predetermined criterion may comprise movement of the asset from an initial location to a new location in two consecutive sets of data and a measurable pathogen contamination in the second of the two consecutive sets of data appearing on a previously clean asset in the new location of the moved asset in the second of the two consecutive sets of data.

In various embodiments, the obtaining, by the computer-based system, a second measure of pathogen contamination for each asset after passage of the prescribed length of time further comprises DNA or RNA sequencing of pathogens. The DNA/RNA sequencing may be performed by a DNA/RNA sequencing unit that is part of an infection control apparatus. In various aspects, the DNA or RNA sequencing of pathogens is used by the computer-based system in the analyzing to determine the extent of mutations between instances of the same organism, how long the organism has existed, how far it has been transferred, and if the pathogen has been physically transferred between any two assets by remaining viable on an asset that has been relocated in the facility.

In various embodiments, disposing, by the computer-based system, a residual self-sanitizing coating composition on each asset identified as a critical control point further comprises at least one of manual spraying, compressed air spraying, electrostatic spraying, and aerosol spraying a surface of each asset identified as a critical control point. The residual self-sanitizing coating composition may comprise at least one of a quaternary ammonium biocide/polymer complex, antimicrobial silver, an organosilane, such as 3-(trimethoxysilyl) propyl dimethyl octadecyl ammonium chloride, or combinations thereof.

In various embodiments, the computer based system comprises an infection control apparatus comprising: an asset tagging unit; a spraying unit; a power supply unit; and a computing unit comprising a non-transitory computer-readable medium encoded with program instructions for controlling the asset tagging unit and the spraying unit to perform the method of infection control in the facility. In various aspects, the program instructions further comprise RFID asset management and tracking software programming.

BRIEF DESCRIPTION OF THE DRAWINGS

The subject matter of the present disclosure is pointed out with particularity and distinctly claimed in the concluding portion of the specification. A more complete understanding of the present disclosure, however, may best be obtained by referring to the detailed description and claims when considered in connection with the following drawing figures:

FIG. 5 sets forth a summary of the microbial burden in a study conducted with 114 stationary assets in the ICU of a prominent medical center.

DETAILED DESCRIPTION

The detailed description of exemplary embodiments herein makes reference to the accompanying drawings, which show exemplary embodiments by way of illustration and their best mode. While these exemplary embodiments are described in sufficient detail to enable those skilled in the art to practice the invention, it should be understood that other embodiments may be realized and that logical, chemical, and mechanical changes may be made without departing from the spirit and scope of the inventions. Thus, the detailed description herein is presented for purposes of illustration only and not of limitation. For example, unless otherwise noted, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option. Additionally, any reference to without contact (or similar phrases) may also include reduced contact or minimal contact.

In various embodiments, a method of infection control in accordance to the present disclosure comprises:

(1) creating, by a computer-based system, an asset record for each of one or more assets within a facility;

(2) tagging, by the computer-based system, each asset with a barcode or RFID tag associated with each asset record;

(3) obtaining, by the computer-based system, a first location for each asset;

(4) obtaining, by the computer-based system, a first measure of pathogen contamination for each asset;

(5) acquiring, by the computer-based system, the first location and a first measure of pathogen contamination for each asset as a first set of data;

(6) obtaining, by the computer-based system, a second location for each asset after passage of a prescribed length of time;

(7) obtaining, by the computer-based system, a second measure of pathogen contamination for each asset after passage of the prescribed length of time;

(8) acquiring, by the computer-based system, the second location and second measure of pathogen contamination for each asset as a second set of data;

(9) analyzing, by the computer-based system, the sets of data to generate a report including a list of assets identified as critical control points; and

(10) disposing, by the computer-based system, a residual self-sanitizing coating composition on each asset identified as a critical control point.

Figure 1:
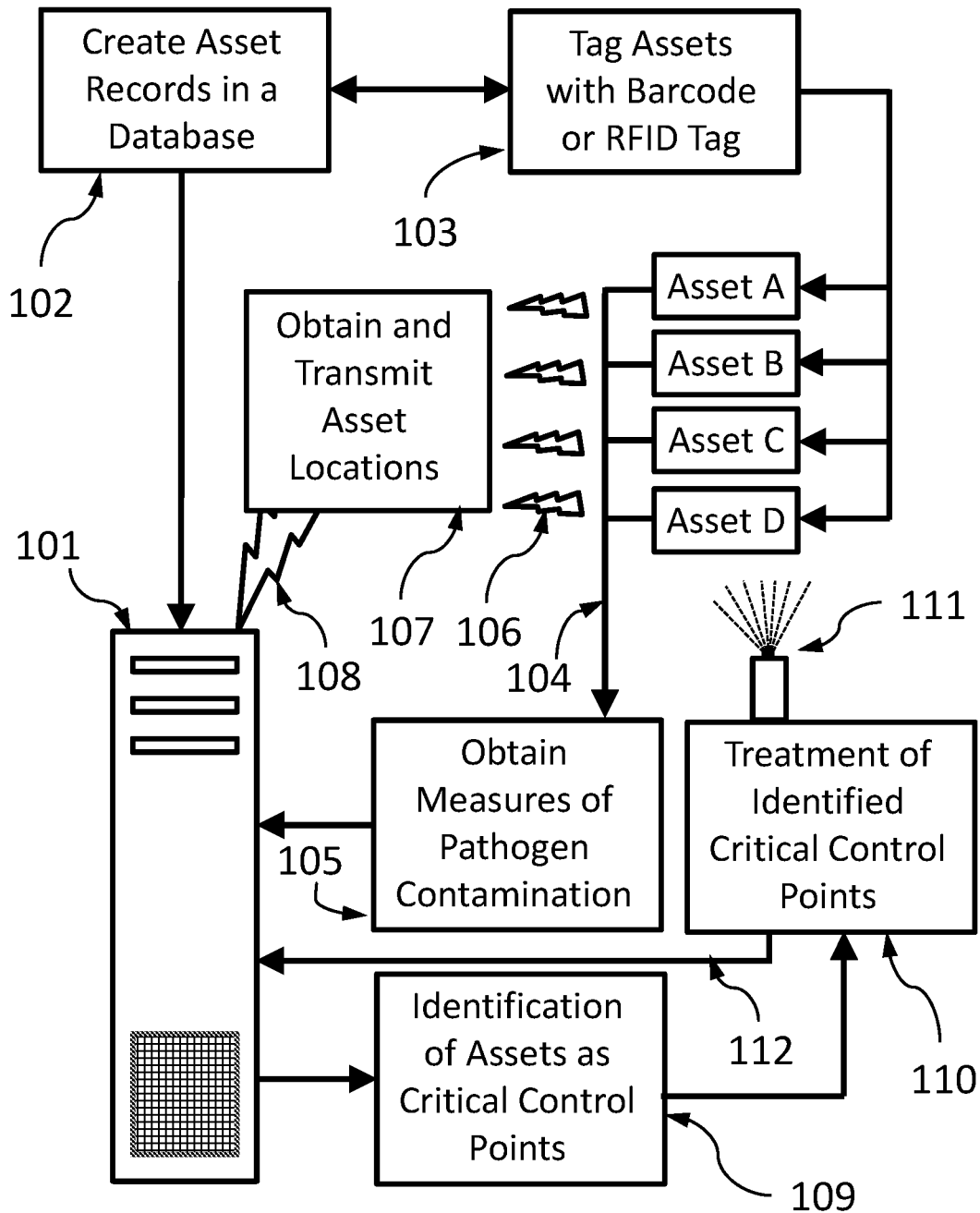
FIG. 1 illustrates a flow chart of an embodiment of an infection control system, further comprising an infection control method and aspects of an infection control apparatus, in accordance with various embodiments.
Figure 2:
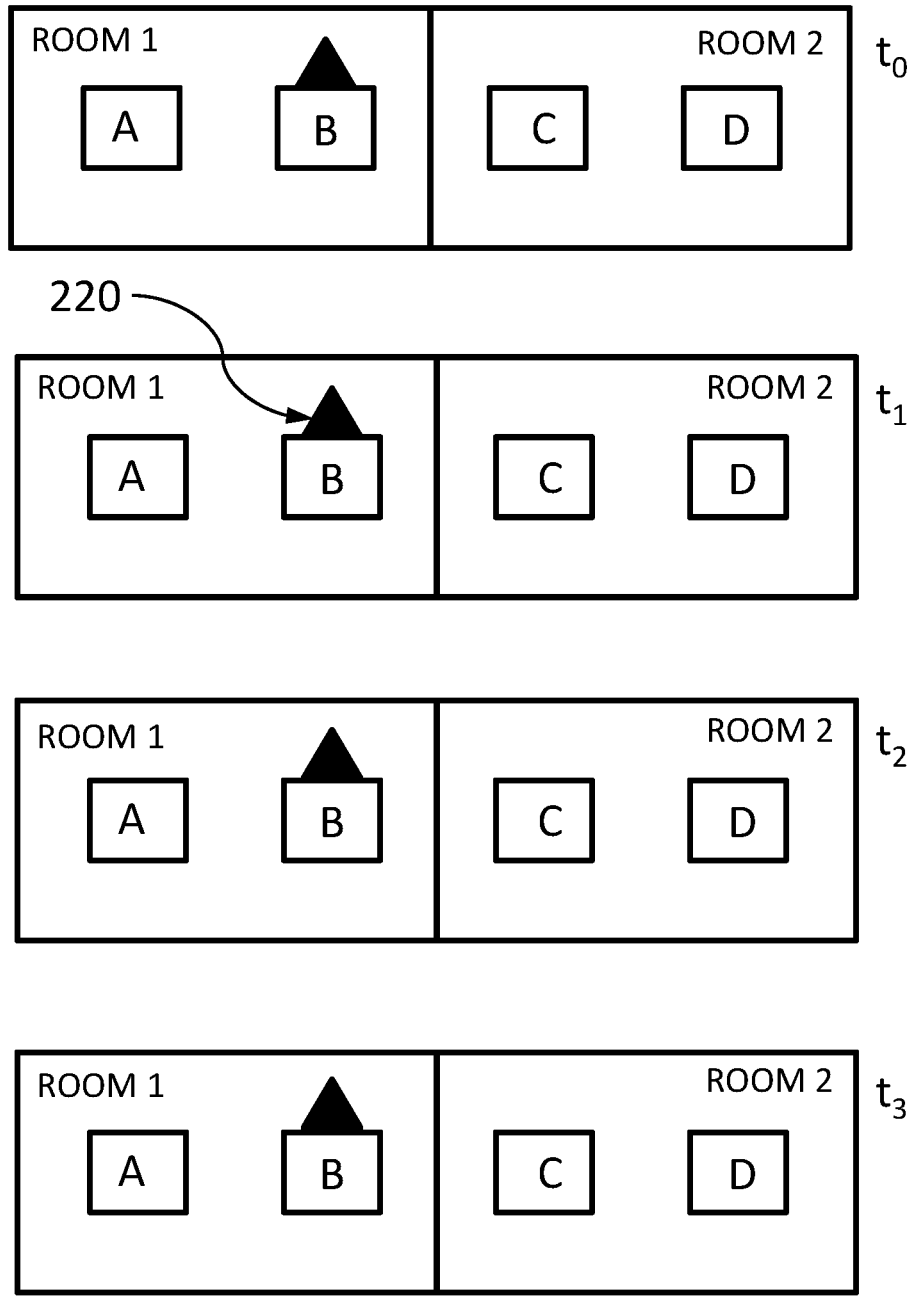
FIGS. 2-4 illustrate hypothetic scenarios of pathogen transfer and asset movement in a facility that may result in certain assets being identified as critical control points, in accordance with various embodiments.

A method of infection control as disclosed herein is at least in part a computer-implemented method and, as such, requires a computer processor or other non-transient computer-readable medium that may be part of a computing unit, which in turn may be part of an infection control apparatus. In various embodiments, a non-transient computer-readable medium is encoded with program instructions that control various units of an apparatus to perform the infection control method herein. In various embodiments, a method of infection control is performed by an infection control apparatus comprising: an asset tagging unit; a spraying unit; a power supply unit; and a computing unit comprising a non-transitory computer-readable medium encoded with program instructions for controlling the asset tagging unit and the spraying unit to perform the present method of infection control in a facility. These units, e.g. the asset tagging unit and the spraying unit, enable performance of various steps of the infection control methods herein. Some steps in the method are performed entirely by program instructions, such as mathematic calculations and determinations. An embodiment of an overall infection control system is illustrated as a flowchart in FIG. 1, showing data acquisition, transfer and storage along with various apparatus units (i.e., hardware, such as a CPU and a spray gun), which will be referred to from time to time as aspects of the method are disclosed. In other words, FIG. 1 illustrates an embodiment of an infection control system that includes both an infection control method and an infection control apparatus.

Methods of infection control in accordance to the present disclosure provide infection control inside facilities (e.g., hospitals) by identifying the critical control surfaces where pathogen transfers occur, and then coating those surfaces with a residual self-sanitizing coating so that the surfaces can no longer sustain viable microorganisms. The method identifies the critical control surfaces by tagging and tracking assets in a facility, monitoring microbial counts and types of microorganisms on the assets over time, and processing these data to identify assets that are the "crossroads" for pathogen transfer. The method further comprises treatment of those surfaces with a residual self-sanitizing coating composition so that the surfaces can no longer participate in pathogen transfer. The method economizes, simplifies and streamlines infectious disease control in a facility by identifying and/or treating only those surfaces determined to be critical control points, so that random, ineffective cleaning and disinfection protocols can be eliminated.

Definitions and Interpretations

As used herein, the term "asset" broadly refers to an object comprising at least one hard inanimate surface (an environmental surface, or fomite), which is located within an interior environment such as a healthcare facility, bus station, train station, airport, restaurant, food service provider, and the like. An asset may be portable and moveable, moveable but never moved or intended to be moved, or entirely fixed and stationary. Assets in a healthcare facility include, for example, beds, carts, trays, IV stands, bedside tables, door handles, portable medical equipment (EKG, X-ray, ultrasound, etc.), reception desk, chair armrests, and countertops.

Assets of interest may include those assets that are frequently touched and/or likely to be contaminated at any particular time. Other assets of interest include those that are moved between patient rooms, such as on a daily basis. Some assets may be so remotely located and so unlikely to be involved in pathogen transfers (e.g. a shelf in an infrequently accessed storage room) that they may not be the target of any pathogen investigation. Assets of high interest are those that are likely to be contaminated, likely to be moved frequently, and/or that are handled frequently or placed into contact with a person, such as a person with an infection. Some assets that come into contact with one patient, such as a portable X-ray machine, are of interest since they could be involved in the movement of pathogens to another patient.

Assets may have a particular surface that is touched or that contacts a person and one or more other surfaces that are never in human contact. For example, a countertop asset will be frequently touched on the top surface and front edge, but rarely if ever underneath. Even though the asset may be of interest since pathogens could be transferred to and from the countertop, only the top surface and front edge may be of interest for microorganism monitoring. Further, some assets may comprise a combination of hard and soft surfaces. One example is a hospital bed that includes the adjustable bedrails, usually metal, which are frequently handled, and the bedding that is laundered and not easily monitored for microorganism presence over time. In this case, the asset is logged-in to the apparatus as "hospital bed," with a note that the surfaces of interest for pathogen transfer may be the metal rails. Another example is a chair, which is an asset having a soft surface (cushion) and hard surfaces (the armrests), and it is the latter that may be the surfaces of interest in pathogen transfer on this asset.

As used herein, the terms "crossroads" and "critical control points" are used interchangeably to refer to those surfaces of assets that are found to be pathogen transfer points. A critical control point may be referenced by the asset name for simplicity, even though only one surface of the asset may be involved in the transfer of pathogens. As discussed herein, the critical control points are then be treated with a residual self-sanitizing coating composition so that they can no longer harbor viable organisms at pathogenic levels. In this way, critical control points, once identified and coated, cease to be pathogen transfer "crossroads."

As used herein, the term "facility" refers to any interior environment of any size. Facilities include, but are not limited to, hospitals and healthcare buildings in general, restaurants, train stations, bus stations, airports, train, bus, plane, food trucks, office buildings, schools, churches, and the like. Although the present disclosure focuses on healthcare facilities such as hospitals, and exemplifies the control of HAIs in a hospital, the present disclosure is not limited to the healthcare industry or HAIs at all, and can easily be adapted to control the spread of infection in any of these other facilities.

As used herein, the term "pathogen" takes on the ordinary and customary meaning of microorganisms that cause infection in a host. Within the scope, pathogens of interest include those that cause human infections, and these generally comprise bacteria, viruses and fungi. Further, pathogens recognized as microorganisms that cause HAIs and known to transfer indirectly through contaminated surfaces are of interest within the scope of the disclosure. For example, pathogens that cause HAIs include, but are not limited to norovirus, poliovirus, rotavirus, influenza virus, adenovirus, *Staphylococcus aureaus*; methicillin resistant *Staphylococcus aureus* (MRSA); vancomycin resistant *Enterococcus* (VRE); carbapenem resistant Enterobacteriacea (CRE); *Listeria* spp.; *Klebsiella* spp.; *Pseudomonas aeruginosa; Acinetobacter* ssp.; *Bacillus anthraces; Salmonella* spp.; *Campylobacter* spp.; *Mycobacterium* spp.; *Streptococcus* spp.; and *Clostridium difficile*. Any one or more of these microorganisms, along with others now known or yet to be identified, may be responsible for infections spread within a facility, and thus controlling growth and spread of such microorganisms within a facility is a way to control infection in the facility.

As used herein, the acronym "CFU" or "CFU's" refers to "colony forming units," which in the field of microbiology refers to individual colonies of microorganisms counted on an agar plate. CFU is a measure of the level of contamination of a surface, whereby an agar plate is inoculated with a dilution of the microorganisms obtained from a test swab previously wiped on the surface to be tested. If the microorganisms are efficiently distributed on the agar plate, it can be generally assumed that each cell will give rise to a single colony, which can be counted. The counting of CFU's on an agar plate may be manual (e.g. assisted by a click-counter so as not to lose count), or may be electronic, such as by electrical resistance, flow cytometry, image analysis, or other method. Electronic methods for counting CFU's may be calibrated by hand counting. The appearance of each colony, (e.g. shape, color), can be indicative of the species of microorganism growing on the plate. Otherwise, a separate genetic test can be used to verify the identity of a pathogen.

As used herein, the term "antimicrobial" is used generally to indicate at least some level of microbial kill by a composition or a coating on a surface of an asset. For example, antimicrobial may be used to indicate a sanitizing level (3-log, or 99.9%) reduction in at least one organism, or a disinfection level (5-log, or 99.999%) reduction in at least one organism, or sterilization (no detectable organisms). Microorganisms may include any species of bacteria, virus, mold, yeast, or spore. The terms "residual antimicrobial," "residual self-sanitizing," and "self-decontaminating surface" are used interchangeably to indicate a hard inanimate environmental surface that maintains antimicrobial efficacy over a certain period of time under certain conditions once the surface is coated with an antimicrobial coating composition. A coated surface may maintain residual antimicrobial efficacy indefinitely, or the coating may eventually "wear out" and lose its residual antimicrobial efficacy. An antimicrobial coating composition may function as a contact sanitizer, disinfectant, or sterilant when first applied to a surface, and also have the ability to leave behind a residual antimicrobial effect on the surface once dried or cured thereon that can keep inactivating new microorganisms that contact the coated surface. In various embodiments, coating compositions may not be antimicrobial until dried or cured on an asset surface, but are still referred to as antimicrobial coating compositions because of their ability to produce a residual antimicrobial coating on a surface. Antimicrobial coating compositions for use in various embodiments may provide a residual antimicrobial efficacy to a surface of an asset, meaning that a microorganism later inoculated on, or that otherwise comes in contact with the coated asset surface, may experience cell death, destruction, or inactivation. The residual antimicrobial effect made possible by the coatings is not limited by a particular mechanism of action, and no such theories are proffered. For example, an antimicrobial effect measured on a surface may be the result of intracellular mutations, inhibition of certain cellular processes, rupture of a cell wall, immobilization and thus prevention of transfer or detection when swabbing, or a nondescript inactivation of the organism. Other antimicrobial effects may include inhibiting the reproduction of an organism, or inhibiting the organism's ability to accumulate into biofilms. In other embodiments, an antimicrobial effect may be a stasis such that organisms cannot proliferate to the point of reaching a pathogenic level on the treated surface.

As used herein, the term "antimicrobial coating composition" or "residual self-sanitizing coating composition" refers to a chemical composition comprising at least one chemical species, which is used to produce a residual self-sanitizing antimicrobial coating on an asset surface after the composition is applied and then either dried, allowed to dry, or cured in some manner. However, the term is extended to include a composition that may be applied sequentially (e.g. over or under) or contemporaneously with the application of an antimicrobial coating composition comprising an antimicrobial active, such as to assist in bonding the residual antimicrobial coating to the surface, improve durability of the overall coating, and/or to provide a catalytic effect or some sort of potentiation or synergy with the residual antimicrobial coating comprising an antimicrobial active. For simplicity herein, each one of multiple compositions used sequentially or contemporaneously to produce an overall residual antimicrobial coating on a medical implement or device is referred to as an "antimicrobial coating composition," even if one or more of the compositions used for coating has no identifiable antimicrobial active or where the active agent is uncertain. An antimicrobial coating composition may comprise a neat, 100% active chemical species or may be a solution or suspension of a single chemical species in a solvent. In other aspects, a composition may comprise a complex mixture of chemical substances, some of which may chemically react (hydrolyze, self-condense, etc.) within the composition to produce identifiable or unidentifiable reaction products. For example, a monomeric chemical species in an antimicrobial coating composition may partially or fully polymerize while in solution prior to a coating process using that composition. In various embodiments, chemical constituents within an antimicrobial coating composition may chemically react on the surface that the composition is applied to, such as while the composition is drying and concentrating on the surface or while the coating composition is cured by various methods. Antimicrobial coating compositions for use in various embodiments may further comprise any number and combination of inert excipients, such as for example, solvents, surfactants, emulsifiers, stabilizers, thickeners, free-radical initiators, catalysts, etc. Exemplary antimicrobial coating compositions that leave behind a residual self-sanitizing coating on a surface, and that are suitable for use herein, include, but are not limited to: a quaternary ammonium biocide/polymer complex exemplified in U.S. Pat. Nos. 6,017,561; 6,080,387; 6,270,754; and 6,482,392 assigned to The Clorox Company and incorporated herein by reference in their entireties; solutions of 3-(trimethoxysilyl) propyl dimethyl octadecyl ammonium chloride (CAS No. 27668-52-6, obtained under various trade names); SilverShield®, a coating that delivers antimicrobial silver over time and is available from Microban®, Huntersville, N.C.; and solutions and methods comprising various organosilanes, organic amines, titanium(IV) species, titanium sols, tartaric acid/titanium complexes, and combinations thereof, as exemplified in U.S. patent application Ser. No. 15/938,417 filed Mar. 28, 2018 and Ser. No. 15/969,576 filed May 2, 2018, both assigned to Allied Bioscience, Inc. and incorporated herein by reference in their entireties; in PCT International Patent Application Serial Nos. PCT/US13/073878; PCT/US15/059080; and PCT/US16/017599 assigned to Allied Bioscience, Inc. and incorporated herein by reference in their entireties; and in U.S. Pat. Nos. 9,963,596; 9,918,475; 9,856,360; 9,855,584; 9,757,769; and 9,528,009, assigned to Allied Bioscience, Inc. and incorporated herein by reference in their entireties. In various embodiments, the infection control apparatus is used to coat an environmental surface with either (a) a mixture of 3-(trimethoxysilyl) propyl dimethyl octadecyl ammonium chloride, 3-chloropropyltrimethoxysilane, and triethanolamine, remainder water; or (b) a mixture of 3-aminopropyltriethoxysilane and triethanolamine, remainder water. Either organosilane coating may be coated overtop with a titanium species, such as an aqueous mixture of $TiO_2$ or a sol that provides a film of $TiO_2$. In other embodiments, an environmental surface is first coated with a titanium species and then with either composition (a) or (b). In other embodiments, any other residual self-sanitizing coating, whether modifications of these quaternary and organosilane technologies, or comprising any other coating technology, are suitable for use in infection control as per the present disclosure.

Computer Processing

In various embodiments, a method of infection control is computer implemented and requires a computer processor (CPU) or other non-transient computer-readable medium that may be part of an overall computing unit having additional components besides the CPU. In certain embodiments, the computing unit may comprise a desktop computer, a laptop computer, a tablet, or a remotely located mainframe computer, such as illustrated in FIG. 1 as CPU 101. The computing unit may further comprise specialized peripherals, such as optical readers for counting the CFU's on an agar plate, or molecular sensors used in genetic sequencing of pathogens. The computing unit comprises both hardware and software along with the necessary connections (hardwire/USB or wireless) to other units that may assist in enabling the method. In particular, program instructions encoded on the non-transient computer-readable medium control an asset tagging unit and any of its components, a spraying unit and any of its components, and an optional DNA/RNA sequencing unit, to perform aspects of the present infection control method. Computing hardware may comprise a computer running on any platform, further comprising a CPU, memory (e.g. RAM and ROM), keyboard, monitor, mouse and peripherals as needed. The computing unit may have its own power supply, or may tap into power available from a centralized power supply unit.

A keyboard and mouse may be used to manually input data into the computer processor, such as inputting the names of each of the assets in a facility, the initial locations of each asset at the start of an infection control procedure, and measures of pathogen contamination of various assets at various times during infection control. Some data will need to be manually entered into the computer processor, such as a list of the assets to be monitored and the measures of pathogen contamination on each asset, whilst other data may be electronically and automatically transmitted from a peripheral device to the computer processor, such as the locations of assets comprising RFID tags sensed by local RFID readers stationed around the facility.

In various embodiments, a computer processor for enabling an infection control method herein further comprises encoded program instructions, i.e., computer software, which may be stored on a local hard drive of the CPU and/or on the Cloud. The software comprises those programs required to perform various steps of the present infection control method. In various embodiments, the software comprises database software capable of managing large sets of data. For example, a database program may provide fields for information regarding each asset in a facility, and these fields may be automatically filled in (e.g. date and time of day), manually filled in (e.g. entering in data from a keyboard), and/or electronically filled in upon a command, (e.g. RFID tag locations in an automated asset inventory procedure). Software may further comprise programs for enabling asset tagging, such as to coordinate barcode scanning with the database asset records, or to operate barcode label printers and/or RFID readers and remote sensors. Software may further comprise asset management and tracking software, which may be a retail software program used in other industries such as shipping and warehousing. In certain embodiments, software may comprise software for enabling a spraying unit, e.g. including a spray module with automated computer controlled valves and sensors, and to enable an optional DNA/RNA sequencing unit. Other software may include network software and algorithms to organize asset data entries and incoming data transfers, facilitate communication between units and modules in an apparatus, and to calculate certain parameters as needed. The computing unit may further comprise software that records spray times from the spraying unit when that unit is actively used for spraying chemicals.

In various embodiments, the CPU further comprises an algorithm to process all the inputted data. Inputted data includes, but is not limited to, the asset tracking data, which is the location of the assets over time, and the microbial data, which comprises measures of pathogen contamination on each asset over time. The measures of microbial contamination of an asset are determined by swabbing surfaces of an asset, performing serial dilutions from the swab, inoculating agar plates, incubating agar plates, and counting CFU's on the plates. The CFU's give a measure of the original contamination that was on the asset surface. This data is likely entered into an asset record manually. Optionally, the microbial data further comprises DNA/RNA sequencing data for particular microorganisms on various assets, obtained for example from a DNA/RNA sequencing unit and transferred to the CPU for analysis.

The computer implemented analysis by the CPU comprises an analysis of data sets (each data set comprising asset location and measure of pathogen contamination on the asset at a particular time) to find those assets meeting predetermined criteria to be categorized as a critical control point within the facility. The algorithm takes into consideration the pathogen counts on assets over time, how the assets moved about the facility over time, and how pathogens in one place in the facility relate genetically and generationally to pathogens found in another place in the facility. When DNA/RNA sequencing is enabled, e.g. through a DNA/RNA sequencing unit, the genetic make-up of the pathogens can be used by the algorithm to determined the extent of mutations between instances of the same organism, and thus how long the organism has existed, how far it has been transferred, and if the pathogen has in fact been physically transferred by remaining viable on an asset that has been relocated in the facility. The CPU generates a report that comprises a list of assets identified as critical control point, i.e. those assets that meet the predetermined criteria. Once the assets are identified as critical control points by the CPU algorithm, then those assets are sprayed with a residual self-sanitizing coating composition by the appropriate spraying unit.

Asset Tagging

In general, a method of infection control comprises tagging assets within a facility so that their positions and movement around a facility can be tracked. Stationary assets may be tagged as well, simply to retain ID of the asset and a record of the changing pathogen levels on the stationary asset. Tracking of assets may be manual (such as by barcodes that require close-up and focused scanning) or real-time (such as by RFID tags), as explained herein. In some aspects, asset tagging comprises an asset management and tracking system further comprising hardware and software, such as used for tool and equipment check-in/check-out inventory, shipping/receiving and warehousing, pallet tracking, and general asset management in many industries. In various embodiments, asset tracking data are entered into or sent to the computer processor where the data are used, in part, to identify the critical control points in a facility, i.e. those surfaces where pathogens are being transferred to and from to cause an infection in the facility.

At the start of implementation of an infection control method, there may be no assets logged into the database of the computer processor. Thus, each asset of interest in infection control in a facility can be logged into the database by name or by description of the asset, optionally including a picture of the asset. This is schematically represented in FIG. 1 as step 102, "create asset records in a database," with indication the information is entered into and stored on the CPU 101. The asset information may be entered into the database using a keyboard. Further information that may be added into each asset record includes, but is not limited to, the shape and size of the asset, the surface area of touched surfaces on the asset, the temperature and relative humidity of the area surrounding the asset initially, and so forth. Then as each asset is physically tagged, such as by attaching a printed barcode or RFID tag onto the asset, a unique identifier such as the barcode number or RFID address can be associated with the asset record in the database. In this way, each asset becomes a record in the database, and additional information can be added to each asset record over time as needed. For example, the initial location of each asset may be entered into the appropriate field of each record as each record is created. An initial measure of pathogen contamination found on the asset can also be entered into each record. The location of the asset and the measure of pathogen contamination on the asset are then updated for each asset after passage of predetermined time periods.

With reference again to FIG. 1, the tagging of assets is represented as method step 103, with the two directional arrows indicating the association between the barcodes and/or RFID addresses and the asset records. As shown in the embodiment of FIG. 1, assets A, B, C, and D are each tagged with a unique barcode, a unique RFID tag, or another form of unique identifier. Initial and subsequent locations of the assets A, B, C, and D are transmitted electronically as signals 106, and these data obtained in step 107 may be transmitted electronically via signals 108 to the CPU 101. These processes can of course be manual, by handheld barcode readers, for example, with the information wirelessly transmitted from the handheld barcode reader to the CPU 101. The automated aspects of updating asset locations via RFID tag location is discussed herein.

In various embodiments, asset tagging may comprise a barcode printer, printable labels, a barcode scanner, and barcode software. Both the hardware (printer, scanner and labels) and the software for asset management are available from, for example, Wasp Barcode Technologies, Inc., Plano, Tex., amongst other suppliers. The barcode software may be stored as encoded program instructions on the computer processor or may be stored, at least in part, on non-transient computer-readable medium within a handheld device such as a barcode reader. In various embodiments a portable barcode printer may be taken to the location of certain assets along with a laptop or tablet, such as when the asset is too large to move (e.g. an X-ray machine) or is stationary (e.g. a countertop at a nurses' station), and/or when computers and equipment (e.g. an infection control apparatus embodied on a cart) cannot be easily moved to the asset (e.g. an obstructed route). In some instances, the asset can be moved for tagging, or apparatus moved to the asset for tagging, or a portable printer and laptop or tablet can be brought around the facility. In various embodiments, one or more barcode labels are printed out and the barcode labels are simply walked over to the asset where they are applied. Barcodes may be applied to inconspicuous places on an asset, such on the underside of a surface, or in a doorframe rather than directly on a doorknob, away from physical contact areas or the areas that may be sprayed with a residual self-sanitizing coating composition.

In various embodiments, asset tagging comprises RFID (radio frequency identification). For example, asset tagging may comprise use of RFID tags (each with an embedded chip and antenna and optional battery), an RFID reader (a transmitter with associated antenna), and RFID asset management software. As per the barcode variation discussed, the RFID software may reside encoded on the computer processor. RFID tagging provides real-time asset tracking 24/7. RFID tags are applied as per the barcodes, e.g. on assets suspected to be pathogen transfer critical control points, away from the frequently touched portions of the assets. In various embodiments, the type of RFID tag for a particular asset may be based, at least in part, on the nature of the asset to be tagged. For example, some tags are designed to survive elevated temperatures, while others are designed for laundered fabrics. A wide variety of RFID tags is available, for example, from HID Global Corporation, Austin Tex., amongst other suppliers.

In various embodiments, RFID tags on tagged assets herein may be active or passive, or any combination of these, such as depending on the location of assets and likelihood the asset may be moved considerable distances across a medical center. A passive RFID tag requires energy sent as RF from a reader, whereas an active RFID tag has its own power source, a battery, and can communicate with a reader at much further distances on its own power. As per the barcodes, the RFID tags can be scanned from time to time to determine where the tagged assets reside in the facility. Unlike barcoding though, a plurality of RFID readers, e.g. with wireless connection to an asset tagging unit of an infection control apparatus, may be positioned in various locations around a facility such that, regardless of where assets may move to in the facility, there will always be an RFID reader nearby to sweep up the signals from the nearby collection of assets. Thus, by way of a command signal from the computer processor, all of the tagged assets in the facility can be inventoried simultaneous by way of the remotely positioned readers without the need for anyone to walk around with portable RFID readers.

In various embodiments, the step of asset tagging comprises hardware and software that is somewhere between barcodes and RFID tags in sophistication and convenience. An example is NFC (near field communication) asset tracking. With NFC, the scanner does not need to focus precisely on a barcode for reading. However, NFC cannot be used at any distance, and groups of assets cannot be scanned at the same time as per RFID. In other instances, asset tagging may comprise any other asset management and tracking system besides barcoding, RFID or NFC.

The system may include or interface with any of the foregoing accounts, devices, and/or a transponder and reader (e.g. RFID reader) in RF communication with the transponder (which may include a fob), or communications between an initiator and a target enabled by near field communications (NFC). Typical devices may include, for example, a key ring, tag, card, cell phone, wristwatch or any such form capable of being presented for interrogation. Moreover, the system, computing unit or device discussed herein may include a "pervasive computing device," which may include a traditionally non-computerized device that is embedded with a computing unit. Examples may include watches, Internet enabled kitchen appliances, restaurant tables embedded with RF readers, wallets or purses with imbedded transponders, etc. Furthermore, a device may have electronic and communications functionality enabled, for example, by: a network of electronic circuitry that is printed or otherwise incorporated onto or within an instrument (and typically referred to as a "smart card"); a fob having a transponder and an RFID reader; and/or near field communication (NFC) technologies. For more information regarding NFC, refer to the following specifications all of which are incorporated by reference herein: ISO/IEC 18092/ECMA-340, Near Field Communication Interface and Protocol-1 (NFCIP-1); ISO/IEC 21481/ECMA-352, Near Field Communication Interface and Protocol-2 (NFCIP-2); and EMV 4.2 available at http://www.emvco.com/default.aspx.

As explained in detail herein, assets in a facility may be portable, such as carts, tray tables, portable X-ray machines, beds, and the like, or may be permanently stationary, such as a countertop at a nurses' station or the doorknob of a lavatory. Assets are tagged as a way to create a record of a surface that may carry pathogens and that may act as transfer points or "crossroads." Thus, considerations such as the frequency an asset is handled or touched can be more important than whether the asset moves. In other words, even a frequently touched stationary countertop may be the crossroads for pathogen transfer, i.e. a "critical control point," and in recognizing that possibility, it is important to tag the countertop as an asset and monitor the extent and identity of pathogen contamination on the countertop over time regardless that the countertop is stationary.

Measurement of Pathogen Contamination

In various embodiments, the infection control method comprises obtaining a measure of the pathogen contamination on each asset. This can be accomplished by swabbing the touched surfaces of an asset using any type of environmental surface sampling and transport swab. Such swabs are usually furnished in a neutralizing buffer and sealed in a vial. The surface under scrutiny is swabbed with the sampling swab, sealed back inside the vial, and then sent to a microbiology laboratory where the sample can be diluted such as through serial dilutions and the latter used to inoculate a number of agar plates. After the agar plates are incubated, the CFU's are counted and a calculation made as the microbial count on the original surface that was swabbed. An exemplary procedure is provided by the CDC, and is entitled "Environmental Hygiene Monitoring—A Guide for Environmental Health Officers," Oct. 5, 2010, Version 3.

Once obtained, the measure of pathogen contamination for the asset is then entered into the database record for that particular asset for the day/time swabbed. Measures of pathogen contamination may be obtained and entered into the database in units of $\log_{10}$ CFU's/cm$^2$, or other suitable units representing number of organisms per unit of surface area. Contamination when found, and depending on the facility and type of microorganism, may be on the order of from about 1 $\log_{10}$ CFU's/cm$^2$ to about 10 $\log_{10}$ CFU's/cm$^2$.

With reference again to FIG. 1, the step of obtaining measures of pathogen contamination on each of assets A, B, C, and D, is illustrated as step 104. Once the CFU data is obtained for each asset of interest, the data may be entered and stored on the CPU 101 as indicated by step 105.

The measure of pathogen contamination initially found on an asset can be recorded as the measure of pathogen contamination at $t_0$. In various embodiments, this information can be manually entered into the appropriate field in the asset record and thus stored on the non-transient computer-readable medium. Environmental surface test swabs may be sent over to the microbiology laboratory present in the very same medical center where the infection control is being implemented. Further information may be added to the asset record, including the identity of the species of microorganisms found on the asset, such as gleaned from the appearance of the agar plate colonies used for the CFU counts or as confirmed by genetic testing.

An optional step in the method of infection control in accordance to various embodiments comprises DNA or RNA sequencing of the pathogens found on an asset. In conjunction with the previous step, if a pathogen is found on an asset, particularly a pathogen known to cause an HAI, then DNA/RNA sequencing may be performed to obtain genetic information regarding the pathogen. DNA/RNA sequencing may be performed onsite such as by employing a portable DNA/RNA sequencing unit, or samples may be sent off site. The measure of pathogen contamination and the genetic sequencing may be performed by the same laboratory. The genetic information may then be entered into the database for the particular asset associated with the contamination.

Asset Locations and Measures and Identities of Pathogen Contamination Over Time

Asset tagging facilitates tracking where the tagged assets are located in the facility at any given time. Once select assets are barcoded or equipped with an RFID tag, the barcodes on the assets may be scanned on a predetermined schedule (such as daily or another schedule, such as after each time period $t_1$, $t_2$, $t_3$, and so forth) and the scanned data used to map where the assets have moved to, if they were moved at all. In various embodiments, rooms in a facility may be inventoried on a particular day and each barcoded asset present in the room scanned so that all the tagged assets can be logged-in as being in that particular room on that particular day. In other examples, an asset barcode may be scanned when the asset is moved, and then scanned again at its destination. The locations of the assets over time are part of data sets stored on the non-transient computer-readable medium for later analysis.

In various embodiments, asset inventory is triggered from the computer processor, by way of the encoded program instructions, wherein the RFID tags are accounted for all at the same time, using remote RF transmitters placed around the facility. A schedule can be created and modified as necessary, including the periodicity for inventory of the assets and swabbing of the surfaces for measures of pathogen contamination. This process is repeated over time as the assets move around the facility. The time period over which data is collected prior to an assessment as to which assets are the critical control points varies. The overall time period for the assessment may be a day or a few days, or a week or a few weeks, or months, or even longer. An analysis of the existing data sets may be performed at any time, and there may be a plurality of data sets obtained over a period of time comprising the infection control study.

Real-time inventory of assets is illustrated in FIG. 1. RF signals from the assets A, B, C, and D may be triggered by remote RFID transmitters, and the locations of the assets obtained in step 107 and transmitted electronically in 108 to the CPU 101. Step 107 may be enabled by a series of RFID transmitters stationed around the facility.

Asset location and measure of pathogen contamination for each of the assets may be performed after the passage of predetermined time periods, such as in accordance to a particular schedule of time periods, beginning with initial location and measure of pathogen contamination at $t_0$, and then again at $t_1$, $t_2$, $t_3$, etc. These time periods may be of any length, such as minutes, hours, 24 hours, days, weeks, or months and are not necessarily the same (i.e., $t_2-t_1$ does not need to equal $t_1-t_0$, and so forth). In various embodiments, data sets comprising location of assets and present measures of pathogen contamination may be obtained on a daily basis (i.e. every 24-hours, such as on a precise schedule). Thus, after 5-days there will be 5 data sets for analysis. At any time period, DNA or RNA sequencing information may be obtained and added to the asset records for particular assets.

For convenience, the initial data points, including asset location, measure of pathogen contamination, and optionally, genetic sequencing, may be referred to, for example, as the "first set of data" or "Data Set 1." Then the data obtained after the passage of a prescribed period of time, such as 24-hours, i.e. at $t_1$, may be referred to, for example, as the "second set of data" or "Data Set 2." Repeating the asset inventory and the measure of pathogen contamination for each asset at multiple time periods, $t_2$, $t_3$, $t_4$, $t_5$, etc., such as every 24 hours, results in a collection of multiple data sets stored on the non-transient computer-readable medium for analysis by program instructions encoded thereon, e.g. an algorithm. Some of the data, such as RFID locations, may be electronically transferred to the computer processor, whereas measures of pathogen contamination and optional genetic sequencing may be manually entered into the computer processor.

In certain embodiments, the appearances of a disease or a sickness in a patient, independent of any pathogen level assessment, may be seen in a healthcare facility during any of the time periods $t_1$, $t_2$, $t_3$, $t_4$, $t_5$, etc. A disease or sickness may be indicative that a pathogen has been transferred from one location to another location, and then transferred to the patient exhibiting the signs of disease or sickness. Culturing a sample from the patient can confirm that the pathogen responsible for the disease or sickness is the same as the pathogen found on the surfaces the patient likely contacted. Thus appearances of a disease or sickness is a visual signal that pathogens may have been transferred, and in some instances, the methods herein can include tracking of disease and sickness as part of the tracking of asset movement and contamination levels on the assets.

Analysis of Data and Determination of Critical Control Points for Spraying

In various embodiments, the infection control method further comprises analyzing, by executing program instructions encoded on the computer processor, the sets of data (Data Set 1 obtained at $t_0$, Data Set 2 obtained at $t_1$, Data Set 3 obtained at $t_2$, Data Set 4 obtained at $t_3$, and so forth) to generate a report that includes a list of the assets classifiable as critical control points. The database including the location of assets over time and the measures of pathogen contamination on the assets over time, along with the optional DNA/RNA sequencing data and species identification, are used by an algorithm encoded on the computer processor to obtain the identity of the assets that are classifiable as transfer points for pathogens and are thus the crossroads in the spread of infection in the facility. The analysis may involve as few as two sets of data, that is, initial asset locations and initial measures of pathogen contamination at $t_0$ and a second set of asset locations and pathogen contamination measurements at $t_1$, or the analysis may involve more than two data sets.

FIG. 1 illustrates the reporting of the assets classified as critical control points from the CPU 101 as step 109. Step 109 may be enabled by a printer that prints out the names of the assets for which the algorithm categorized as critical control points.

The criteria for the computer implemented determination of what constitutes a critical control point may vary as needed, based on such factors as the nature of the facility (e.g. healthcare versus foodservice), the history of illnesses seen at the facility, and other considerations. The CPU 101 may be reprogrammed to change criteria the algorithm uses to categorize assets as critical control points. FIGS. 2-4 illustrate hypothetic scenarios that provide information to classify particular assets as critical control points. However, these are only a few illustrations of many possible scenarios. In some embodiments, an asset, regardless of its movement or stationary status in the facility, may be deemed a critical control point if it has a measurable pathogen contamination on two consecutive data collection times, such as at $t_0$ and $t_1$, indicating the asset wasn't cleaned properly, may never be cleaned properly, and could perhaps be involved in pathogen transfer and spread of infection in the future. Thus, such an asset having fit the criteria for assignment as a critical control point can be identified as such in a report provided by the computer processor. The asset may then be destined for the step of coating with a residual self-sanitizing composition such that it can no longer sustain viable pathogens.

This scenario is illustrated in FIG. 2, where asset B maintains a pathogen contamination 220 at least at the two time points of $t_0$ and $t_1$. With criteria set this way, the algorithm of the CPU 101 will identify asset B as a critical control point, and asset B should be sprayed with a residual self-sanitizing coating composition as part of the infection control method so that it is taken out as a potential pathogen transfer point.

In various embodiments, the criteria whether an asset is classifiable as a critical control point may be whether the asset moved and a measurable pathogen contamination appeared on a previously clean asset in the new location of the moved asset. In this scenario, the asset moved with a pathogen contamination and then someone likely touched the contaminated asset and transferred pathogens to the other asset. Thus, the asset that moved may be deemed a critical control point, having been determined by the algorithm to fit the criteria. The asset may then be destined for coating with a residual self-sanitizing composition such that it can no longer sustain viable pathogens.

Figure 3:
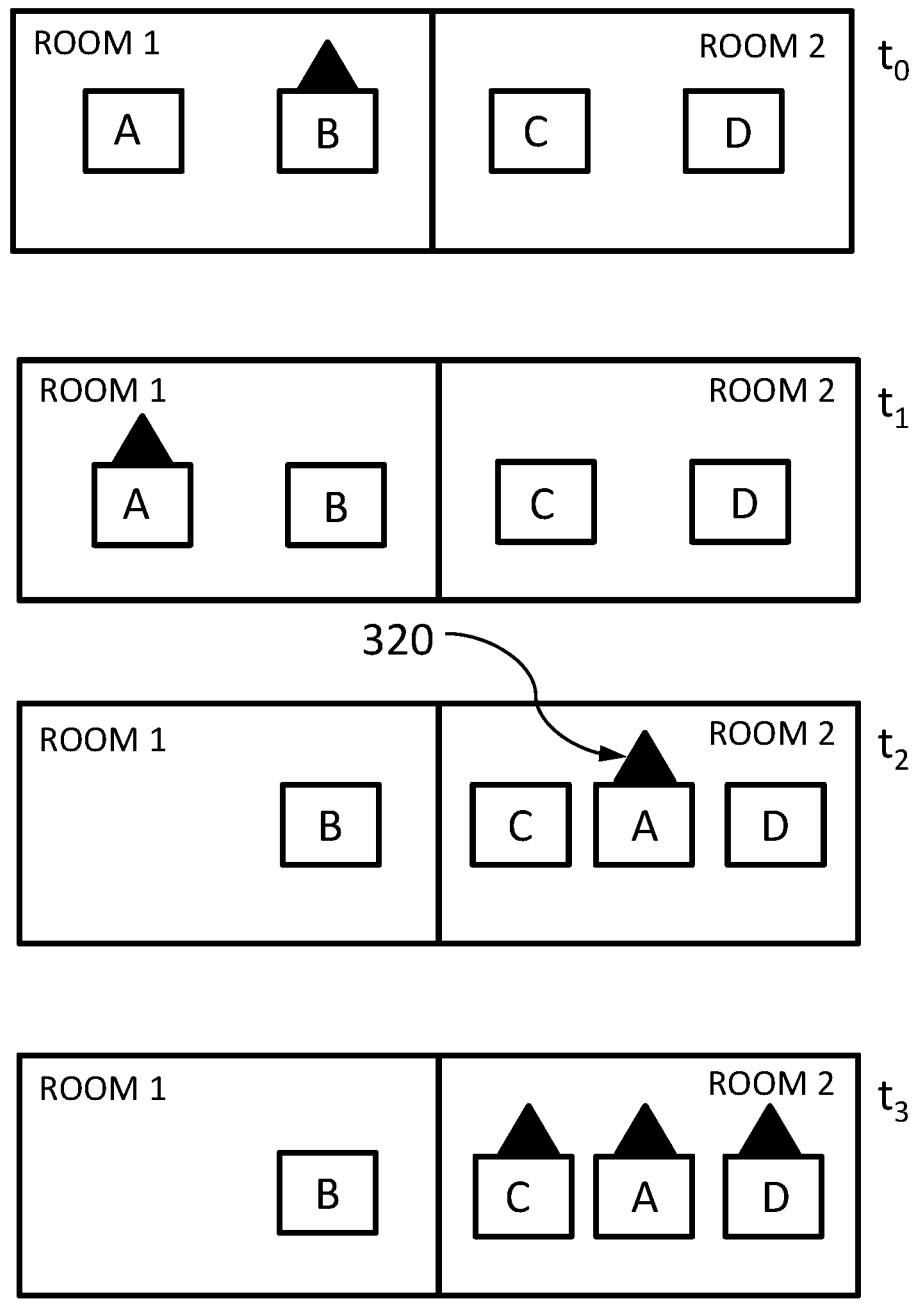

This scenario is illustrated in FIG. 3, where asset A was moved from Room 1 to Room 2 where the pathogen contamination 320 was spread to asset C and asset D. Genetic testing will confirm that the pathogens now found on assets C and D came from the fomite A, rather than from an infected person. With criteria set this way, the algorithm of the CPU 101 will identify asset A as a critical control point, and asset A should be sprayed as part of the infection control method with a residual self-sanitizing coating composition so that it is taken out as a potential pathogen transfer point. In this hypothetical scenario, asset B is seen to be properly cleaned, whereas asset A may have been moved between rooms prior to it being cleaned.

Genetic testing aids the computer implemented decision making as to what constitutes a critical control point, because an organism that appears new within the facility, and determined to not be generationally related to another pathogen also found in the facility, wasn't likely transferred by the asset found contaminated, but instead likely came into the facility via an infected person. Thus the asset the pathogen was found on may not be deemed a critical control point. Further, at the next data collection time, the asset may be found to no longer harbor this pathogen, meaning the asset was properly cleaned and not a critical control point.

Figure 4:
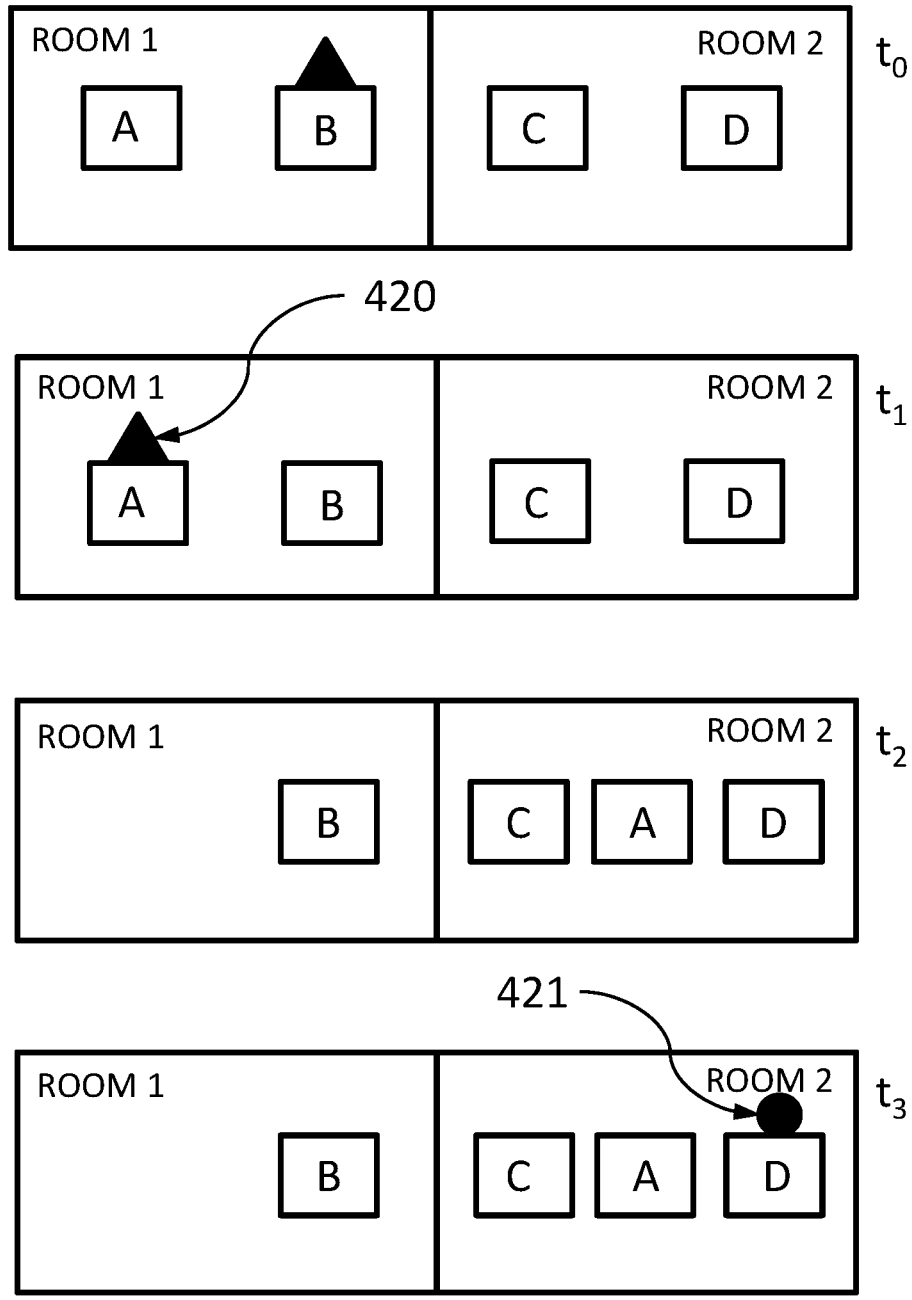

The scenario of pathogens that are not generationally related and appearing on various assets in a facility is illustrated in FIG. 4. In this scenario, there was measureable contamination of asset A with pathogen 420 at time $t_1$. A pathogen 421 of the same species was found on asset D at time $t_3$. However, genetic sequencing determined that pathogen 421 was not generationally descended from pathogen 420, even though they are the same species of pathogen. The conclusion was that asset A did not carry this species of pathogen from Room 1 to Room 2. Thus, with the criteria set this way, none of the assets A, B, C or D are identified by the algorithm as critical control points. Further, the appearance of pathogen 420 on asset B and not on asset A at $t_0$ and then on asset A but not on asset B at time $t_1$, may be evidence that assets A and B were both placed into contact with a person in Room 1 infected with pathogen 420, rather than evidence of transfer of pathogen 420 from asset B to asset A.

Treatment of Assets Identified as Critical Control Points

In various embodiments, the infection control method comprises a step of disposing a residual self-sanitizing coating composition on each asset previously identified as a critical control point, such as by spraying. This step in the infection control method is illustrated in FIG. 1 as step 110, the "treatment of identified critical control points." The disposing of a chemical composition onto a surface of an asset may be by any application method, such as for example, by spraying. Spraying as a treatment method is diagrammatically illustrated in FIG. 1 by sprayer 111 spraying a residual self-sanitizing coating composition onto assets A, B, C, and/or D previously identified as critical control points. Spraying of assets identified as critical control points may comprise any one of manual spraying, compressed air spraying, electrostatic spraying, and aerosol spraying. Spraying of assets may be further enabled by employing a tank module having chemical supply tanks and a spray module in fluid communication with the tank module. In general, the tank module may be used to store and supply chemicals to the spray module, and the spray module may be used to spray chemicals from the tanks onto the previously identified critical control points. Both a spraying module and a tank module may be part of a spraying unit that is further part of an infection control apparatus. In this way, the spraying unit of the infection control apparatus performs the step of treating the identified critical control points in the infection control method. The residual self-sanitizing coating mitigates or eliminates pathogen growth on the asset.

As an asset is treated, the duration of spraying and any one of the rate of spray, the decrease in the weight of a tank of chemicals, and the level of liquid in the tank, may be recorded, and this information sent to the computer processor and stored there. Regardless of the mode of spraying used, various on/off sensors and switches, weight sensors, liquid level floats, optical sensors, and the like, may be employed to enable recordation of chemical spray times and/or the amount of material dispensed from a tank during a spraying session. A report furnished by the computer processor may allow an operator to know how much composition was applied to a particular surface. Further, environmental conditions such as temperature and relative humidity may be recorded at the same time, since these and other conditions may affect the dry times for particular residual self-sanitizing coating compositions. At this time, an operator may enter into the database the surface area of the asset surface being treated and which compositions are applied. Other data, such as the spray times and amounts of materials sprayed may be automatically recorded in the database, some being transmitted wirelessly. Transfer of data relating to asset treatment (chemical spray times, amount of chemicals dispensed, etc.) is diagrammatically illustrated in FIG. 1 as data entry 112 to the CPU 112 from step 110, the treatment of identified critical control points.

When an asset is sprayed with a residual self-sanitizing coating composition, the computer processor may provide a measure of the weight of composition applied per unit of surface area for the particular asset. The units for degree of coating may be $mg/cm^2$ or any other suitable units that indicate how much product has been sprayed on the asset surfaces per unit of surface area. Although these real-time measurements refer to the "wet" composition, the computer processor may calculate the expected weight of dry coating as weight per unit surface area based on the known actives percent of the composition sprayed. That is, data regarding the percent volatiles for a particular composition can be entered into the computer processor such that when an asset is sprayed, the computer processor can provide both the amount of material sprayed in real time (the "wet" amount) and the amount of dried coating expected on the asset once the surface dries, (i.e. by multiplying the amount of wet composition sprayed per unit of surface area times the percent actives of the composition).

In various embodiments, and depending on the particular technology used for residual self-sanitizing coatings, the concentrations of the various compositions used, the type of spraying or other application method, and other considerations, the coating of a surface of an asset identified as a critical control point may be from about 1 $\mu g/cm^2$ up to about 500 $mg/cm^2$ of asset surface, after surfaces are allowed to dry.

After the previously classified critical control points are coated with the appropriate residual self-sanitizing coating, the tracking of assets and the swabbing of pathogens on treated assets (and optionally also on untreated assets) can be continued out through additional time periods (weeks, months or a year, for example), and the assessments at future times will be indicative of the veracity of the procedure. For example, it may be found that previously heavily contaminated and trafficked surfaces of assets no longer harbor pathogenic levels of organisms, and that pathogens are no longer transferred along their previous routes. In various embodiments, previously coated asset surfaces may be tested for efficacy of the coating and/or the presence of coating, and recoated as necessary, knowing that these assets were previously classified as critical control points. In these scenarios, the computing unit of the infection control apparatus may again be engaged in recording a particular recoating schedule of assets.

The veracity of the infection control method disclosed herein may also be demonstrated by tracking HAIs in the subject medical facility. For example, HAIs per quarter or annually may be seen to drop during time periods when critical control assets are coated with residual self-sanitizing coatings.

EXAMPLES

The method of infection control disclosed herein was demonstrated in a large medical center located in Dallas, Tex.

Example 1: Stationary Assets in an ICU

The stationary assets chosen for monitoring were located in each of 24 patient rooms, each of 3 nurses' stations, each of 3 staff lounges, and each of 3 waiting rooms, for a total of 114 assets.

In each one of the 24 patient rooms, there were four assets monitored, namely the wall above the backsplash of the nurses sink, a bed rail, the TV remote and an arm rest of the patient's chair (or alternatively if no chair, the couch). Thus, a total of 96 assets in patient rooms were monitored. The 24 rooms were identified by room number: 4000, 4002, 4012, 4017, 4026, 4032, 4035, 4038, 4201, 4204, 4207, 4218, 4224, 4230, 4233, 4236, 5202, 5203, 5205, 5207, 5209, 5210, 5211, and 5231.

Each of the 3 nurses stations, namely nurses station ICU (4200's), nurses station Neuro ICU (5200's), and nurses station Schenkel (4000's), had two assets for monitoring, the nurses station counter upper and nurses station counter lower. Thus a total of 6 assets in the nurses' stations were monitored.

Each of the 3 staff lounges, namely staff lounge ICU (4200's), staff lounge Neuro ICU (5200's), and staff lounge Schenkel (4000's), had two assets for monitoring, all countertops. Thus a total of 6 assets in the staff lounges were monitored.

Each of the 3 waiting rooms, namely waiting room ICU (4200's), waiting room Neuro ICU (5200's), and waiting room Schenkel (4000's), had two assets for monitoring, the table and an arm rest. Thus a total of 6 assets in the waiting rooms were monitored.

Thus, a total of 114 stationary assets were monitored in the study of Example 1. These assets were declared critical control points simply based on the frequency at which these assets were touched. As noted above, one criterion for classifying an asset as a critical control point for treatment is the frequency at which the asset is touched, regardless if the asset is stationary.

Assets were treated with a composition comprising 3-(trimethoxysilyl) propyl dimethyl octadecyl ammonium initially over a period of about 1 month, then again about 3 months later, and then a third time about 1 month later. Microbial burden on these assets were determined prior to any surface coating, (i.e., at $t_0$), then at 4- and 11-weeks post first treatment, then at 11-weeks post second treatment, and lastly 19 weeks post third treatment. FIG. 5 summarizes the microbial burden on the 114 assets within the medical center. As evident from the summary data, levels of potential pathogens were kept to low levels by the residual self-sanitizing coating on the assets.

In the detailed description, references to "various embodiments", "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

As used herein, "satisfy", "meet", "match", "associated with" or similar phrases may include an identical match, a partial match, meeting certain criteria, matching a subset of data, a correlation, satisfying certain criteria, a correspondence, an association, an algorithmic relationship and/or the like.

Terms and phrases similar to "associate" and/or "associating" may include tagging, flagging, correlating, using a look-up table or any other method or system for indicating or creating a relationship between elements, such as, for example, (i) an account and (ii) a healthcare asset and/or digital channel. Moreover, the associating may occur at any point, in response to any suitable action, event, or period of time. The associating may occur at pre-determined intervals, periodic, randomly, once, more than once, or in response to a suitable request or action. Any of the information may be distributed and/or accessed via a software enabled link, wherein the link may be sent via an email, text, post, social network input and/or any other method known in the art.

The system or any components may integrate with system integration technology such as, for example, the ALEXA system developed by AMAZON. Alexa is a cloud-based voice service that can help you with tasks, entertainment, general information and more. All Amazon Alexa devices, such as the Amazon Echo, Amazon Dot, Amazon Tap and Amazon Fire TV, have access to the Alexa Voice Service. The system may receive voice commands via its voice activation technology, and activate other functions, control smart devices and/or gather information. For example, music, emails, texts, calling, questions answered, home improvement information, smart home communication/activation, games, shopping, making to-do lists, setting alarms, streaming podcasts, playing audiobooks, and providing weather, traffic, and other real time information, such as news. The system may allow the user to access information about eligible accounts linked to an online account across all Alexa-enabled devices.

As used herein, big data may refer to partially or fully structured, semi-structured, or unstructured data sets including millions of rows and hundreds of thousands of columns. Big data sets may be compiled without descriptive metadata such as column types, counts, percentiles, or other interpretive-aid data points.

Distributed computing cluster may be, for example, a Hadoop® cluster configured to process and store big data sets with some of nodes comprising a distributed storage system and some of nodes comprising a distributed processing system. In that regard, distributed computing cluster may be configured to support a Hadoop® distributed file system (HDFS) as specified by the Apache Software Foundation at http://hadoop.apache.org/docs/. For more information on big data management systems, see U.S. Ser. No. 14/944,902 titled INTEGRATED BIG DATA INTERFACE FOR MULTIPLE STORAGE TYPES and filed on Nov. 18, 2015; U.S. Ser. No. 14/944,979 titled SYSTEM AND METHOD FOR READING AND WRITING TO BIG DATA STORAGE FORMATS and filed on Nov. 18, 2015; U.S. Ser. No. 14/945,032 titled SYSTEM AND METHOD FOR CREATING, TRACKING, AND MAINTAINING BIG DATA USE CASES and filed on Nov. 18, 2015; U.S. Ser. No. 14/944,849 titled SYSTEM AND METHOD FOR AUTOMATICALLY CAPTURING AND RECORDING LINEAGE DATA FOR BIG DATA RECORDS and filed on Nov. 18, 2015; U.S. Ser. No. 14/944,898 titled SYSTEMS AND METHODS FOR TRACKING SENSITIVE DATA IN A BIG DATA ENVIRONMENT and filed on Nov. 18, 2015; and U.S. Ser. No. 14/944,961 titled SYSTEM AND METHOD TRANSFORMING SOURCE DATA INTO OUTPUT DATA IN BIG DATA ENVIRONMENTS and filed on Nov. 18, 2015, the contents of each of which are herein incorporated by reference in their entirety.

Any communication, transmission and/or channel discussed herein may include any system or method for delivering content (e.g. data, information, metadata, etc), and/or the content itself. The content may be presented in any form or medium, and in various embodiments, the content may be delivered electronically and/or capable of being presented electronically. For example, a channel may comprise a website or device (e.g., Facebook, YOUTUBE®, APPLE® TV®, PANDORA®, XBOX®, SONY® PLAYSTATION®), a uniform resource locator ("URL"), a document (e.g., a MICROSOFT® Word® document, a MICROSOFT® Excel® document, an ADOBE®.pdf document, etc.), an "ebook," an "emagazine," an application or microapplication (as described herein), an SMS or other type of text message, an email, facebook, twitter, MMS and/or other type of communication technology. In various embodiments, a channel may be hosted or provided by a data partner. In various embodiments, the distribution channel may comprise at least one of a merchant website, a social media website, affiliate or partner websites, an external vendor, a mobile device communication, social media network and/or location based service. Distribution channels may include at least one of a merchant website, a social media site, affiliate or partner websites, an external vendor, and a mobile device communication. Examples of social media sites include FACEBOOK®, FOURSQUARE®, TWITTER®, MYSPACE®, LINKEDIN®, and the like. Examples of affiliate or partner websites include AMERICAN EXPRESS®, GROUPON®, LIVINGSOCIAL®, and the like. Moreover, examples of mobile device communications include texting, email, and mobile applications for smartphones.

In various embodiments, the methods described herein are implemented using the various particular machines described herein. The methods described herein may be implemented using the below particular machines, and those hereinafter developed, in any suitable combination, as would be appreciated immediately by one skilled in the art. Further, as is unambiguous from this disclosure, the methods described herein may result in various transformations of certain articles.

For the sake of brevity, conventional data networking, application development and other functional aspects of the systems (and components of the individual operating components of the systems) may not be described in detail herein. Furthermore, the connecting lines shown in the various figures contained herein are intended to represent exemplary functional relationships and/or physical couplings between the various elements. It should be noted that many alternative or additional functional relationships or physical connections may be present in a practical system.

The various system components discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various databases used herein may include: client data; merchant data; patient data; hospital data; germ data and/or like data useful in the operation of the system. As those skilled in the art will appreciate, user computer may include an operating system (e.g., WINDOWS®, OS2, UNIX®, LINUX®, SOLARIS®, MacOS, etc.) as well as various conventional support software and drivers typically associated with computers.

The present system or any part(s) or function(s) thereof may be implemented using hardware, software or a combination thereof and may be implemented in one or more computer systems or other processing systems. However, the manipulations performed by embodiments were often referred to in terms, such as matching or selecting, which are commonly associated with mental operations performed by a human operator. No such capability of a human operator is necessary, or desirable in most cases, in any of the operations described herein. Rather, the operations may be machine operations. Useful machines for performing the various embodiments include general purpose digital computers or similar devices.

In fact, in various embodiments, the embodiments are directed toward one or more computer systems capable of carrying out the functionality described herein. The computer system includes one or more processors, such as processor. The processor is connected to a communication infrastructure (e.g., a communications bus, cross-over bar, or network). Various software embodiments are described in terms of this exemplary computer system. After reading this description, it will become apparent to a person skilled in the relevant art(s) how to implement various embodiments using other computer systems and/or architectures. Computer system can include a display interface that forwards graphics, text, and other data from the communication infrastructure (or from a frame buffer not shown) for display on a display unit.

Computer system also includes a main memory, such as for example random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a well-known manner. Removable storage unit represents a floppy disk, magnetic tape, optical disk, etc. which is read by and written to by removable storage drive. As will be appreciated, the removable storage unit includes a computer usable storage medium having stored therein computer software and/or data.

In various embodiments, secondary memory may include other similar devices for allowing computer programs or other instructions to be loaded into computer system. Such devices may include, for example, a removable storage unit and an interface. Examples of such may include a program cartridge and cartridge interface (such as that found in video game devices), a removable memory chip (such as an erasable programmable read only memory (EPROM), or programmable read only memory (PROM)) and associated socket, and other removable storage units and interfaces, which allow software and data to be transferred from the removable storage unit to computer system.

Computer system may also include a communications interface. Communications interface allows software and data to be transferred between computer system and external devices. Examples of communications interface may include a modem, a network interface (such as an Ethernet card), a communications port, a Personal Computer Memory Card International Association (PCMCIA) slot and card, etc. Software and data transferred via communications interface are in the form of signals which may be electronic, electromagnetic, optical or other signals capable of being received by communications interface. These signals are provided to communications interface via a communications path (e.g., channel). This channel carries signals and may be implemented using wire, cable, fiber optics, a telephone line, a cellular link, a radio frequency (RF) link, wireless and other communications channels.

The terms "computer program medium" and "computer usable medium" and "computer readable medium" are used to generally refer to media such as removable storage drive and a hard disk installed in hard disk drive. These computer program products provide software to computer system.

Computer programs (also referred to as computer control logic) are stored in main memory and/or secondary memory. Computer programs may also be received via communications interface. Such computer programs, when executed, enable the computer system to perform the features as discussed herein. In particular, the computer programs, when executed, enable the processor to perform the features of various embodiments. Accordingly, such computer programs represent controllers of the computer system.

In various embodiments, software may be stored in a computer program product and loaded into computer system using removable storage drive, hard disk drive or communications interface. The control logic (software), when executed by the processor, causes the processor to perform the functions of various embodiments as described herein. In various embodiments, hardware components such as application specific integrated circuits (ASICs). Implementation of the hardware state machine so as to perform the functions described herein will be apparent to persons skilled in the relevant art(s).

In various embodiments, the server may include application servers (e.g. WEB SPHERE, WEB LOGIC, JBOSS, EDB® Postgres Plus Advanced Server® (PPAS), etc.). In various embodiments, the server may include web servers (e.g. APACHE, IIS, GWS, SUN JAVA® SYSTEM WEB SERVER, JAVA Virtual Machine running on LINUX or WINDOWS).

A web client includes any device (e.g., personal computer) which communicates via any network, for example such as those discussed herein. Such browser applications comprise Internet browsing software installed within a computing unit or a system to conduct other communications or germ mapping. These computing units or systems may take the form of a computer or set of computers, although other types of computing units or systems may be used, including laptops, notebooks, tablets, hand held computers, personal digital assistants, set-top boxes, workstations, computer-servers, main frame computers, mini-computers, PC servers, pervasive computers, network sets of computers, personal computers, such as IPADS®, IMACS®, and MAC-BOOKS®, kiosks, terminals, point of sale (POS) devices and/or terminals, televisions, or any other device capable of receiving data over a network. A web-client may run MICROSOFT® INTERNET EXPLORER®, MOZILLA® FIREFOX®, GOOGLE® CHROME®, APPLE® Safari, or any other of the myriad software packages available for browsing the internet.

Practitioners will appreciate that a web client may or may not be in direct contact with an application server. For example, a web client may access the services of an application server through another server and/or hardware component, which may have a direct or indirect connection to an Internet server. For example, a web client may communicate with an application server via a load balancer. In various embodiments, access is through a network or the Internet through a commercially-available web-browser software package.

As those skilled in the art will appreciate, a web client includes an operating system (e.g., WINDOWS®/CE/Mobile, OS2, UNIX®, LINUX®, SOLARIS®, MacOS, etc.) as well as various conventional support software and drivers typically associated with computers. A web client may include any suitable personal computer, network computer, workstation, personal digital assistant, cellular phone, smart phone, minicomputer, mainframe or the like. A web client can be in a home or business environment with access to a network. In various embodiments, access is through a network or the Internet through a commercially available web-browser software package. A web client may implement security protocols such as Secure Sockets Layer (SSL) and Transport Layer Security (TLS). A web client may implement several application layer protocols including http, https, ftp, and sftp.

In various embodiments, components, modules, and/or engines of a system may be implemented as micro-applications or micro-apps. Micro-apps are typically deployed in the context of a mobile operating system, including for example, a WINDOWS® mobile operating system, an ANDROID® Operating System, APPLE® IOS®, a BLACKBERRY® operating system and the like. The micro-app may be configured to leverage the resources of the larger operating system and associated hardware via a set of predetermined rules which govern the operations of various operating systems and hardware resources. For example, where a micro-app desires to communicate with a device or network other than the mobile device or mobile operating system, the micro-app may leverage the communication protocol of the operating system and associated device hardware under the predetermined rules of the mobile operating system. Moreover, where the micro-app desires an input from a user, the micro-app may be configured to request a response from the operating system which monitors various hardware components and then communicates a detected input from the hardware to the micro-app.

As used herein, the term "network" includes any cloud, cloud computing system or electronic communications system or method which incorporates hardware and/or software components. Communication among the parties may be accomplished through any suitable communication channels, such as, for example, a telephone network, an extranet, an intranet, Internet, point of interaction device (point of sale device, personal digital assistant (e.g., IPHONE®, BLACK-BERRY®), cellular phone, kiosk, etc.), online communications, satellite communications, off-line communications, wireless communications, transponder communications, local area network (LAN), wide area network (WAN), virtual private network (VPN), networked or linked devices, keyboard, mouse and/or any suitable communication or data input modality. Moreover, although the system is frequently described herein as being implemented with TCP/IP communications protocols, the system may also be implemented using IPX, APPLE® talk, IP-6, NetBIOS®, OSI, any tunneling protocol (e.g. IPsec, SSH), or any number of existing or future protocols. If the network is in the nature of a public network, such as the Internet, it may be advantageous to presume the network to be insecure and open to eavesdroppers. Specific information related to the protocols, standards, and application software utilized in connection with the Internet is generally known to those skilled in the art and, as such, need not be detailed herein. See, for example, DILIP NAIK, INTERNET STANDARDS AND PROTOCOLS (1998); JAVA® 2 COMPLETE, various authors, (Sybex 1999); DEBORAH RAY AND ERIC RAY, MASTERING HTML 4.0 (1997); and LOSHIN, TCP/IP CLEARLY EXPLAINED (1997) and DAVID GOURLEY AND BRIAN TOTTY, HTTP, THE DEFINITIVE GUIDE (2002), the contents of which are hereby incorporated by reference.

The various system components may be independently, separately or collectively suitably coupled to the network via data links which includes, for example, a connection to an Internet Service Provider (ISP) over the local loop as is typically used in connection with standard modem communication, cable modem, Dish Networks®, ISDN, Digital Subscriber Line (DSL), or various wireless communication methods, see, e.g., GILBERT HELD, UNDERSTANDING DATA COMMUNICATIONS (1996), which is hereby incorporated by reference. It is noted that the network may be implemented as other types of networks, such as an interactive television (ITV) network. Moreover, the system contemplates the use, sale or distribution of any goods, services or information over any network having similar functionality described herein.

"Cloud" or "Cloud computing" includes a model for enabling convenient, on-demand network access to a shared pool of configurable computing resources (e.g., networks, servers, storage, applications, and services) that can be rapidly provisioned and released with minimal management effort or service provider interaction. Cloud computing may include location-independent computing, whereby shared servers provide resources, software, and data to computers and other devices on demand. For more information regarding cloud computing, see the NIST's (National Institute of Standards and Technology) definition of cloud computing at http://csrc.nist.gov/publications/nistpubs/800-145/SP800-145.pdf (last visited June 2012), which is hereby incorporated by reference in its entirety.

The system contemplates uses in association with web services, utility computing, pervasive and individualized computing, security and identity solutions, autonomic computing, cloud computing, commodity computing, mobility and wireless solutions, open source, biometrics, grid computing and/or mesh computing.

Any databases discussed herein may include relational, hierarchical, graphical, blockchain, object-oriented structure and/or any other database configurations. Common database products that may be used to implement the databases include DB2 by IBM® (Armonk, N.Y.), various database products available from ORACLE® Corporation (Redwood Shores, Calif.), MICROSOFT® Access® or MICROSOFT® SQL Server® by MICROSOFT® Corporation (Redmond, Wash.), MySQL by MySQL AB (Uppsala, Sweden), MongoDB®, Redis®, Apache Cassandra®, or any other suitable database product. Moreover, the databases may be organized in any suitable manner, for example, as data tables or lookup tables. Each record may be a single file, a series of files, a linked series of data fields or any other data structure.

The blockchain structure may include a distributed database that maintains a growing list of data records. The blockchain may provide enhanced security because each block may hold individual data elements and the results of any blockchain executables. Each block may contain a timestamp and a link to a previous block. Blocks may be linked because each block may include the hash of the prior block in the blockchain. The linked blocks form a chain, with only one successor block allowed to link to one other predecessor block.

Association of certain data may be accomplished through any desired data association technique such as those known or practiced in the art. For example, the association may be accomplished either manually or automatically. Automatic association techniques may include, for example, a database search, a database merge, GREP, AGREP, SQL, using a key field in the tables to speed searches, sequential searches through all the tables and files, sorting records in the file according to a known order to simplify lookup, and/or the like. The association step may be accomplished by a database merge function, for example, using a "key field" in pre-selected databases or data sectors. Various database tuning steps are contemplated to optimize database performance. For example, frequently used files such as indexes may be placed on separate file systems to reduce In/Out ("I/O") bottlenecks.

More particularly, a "key field" partitions the database according to the high-level class of objects defined by the key field. For example, certain types of data may be designated as a key field in a plurality of related data tables and the data tables may then be linked on the basis of the type of data in the key field. The data corresponding to the key field in each of the linked data tables is preferably the same or of the same type. However, data tables having similar, though not identical, data in the key fields may also be linked by using AGREP, for example. In accordance with one embodiment, any suitable data storage technique may be utilized to store data without a standard format. Data sets may be stored using any suitable technique, including, for example, storing individual files using an ISO/IEC 7816-4 file structure; implementing a domain whereby a dedicated file is selected that exposes one or more elementary files containing one or more data sets; using data sets stored in individual files using a hierarchical filing system; data sets stored as records in a single file (including compression, SQL accessible, hashed via one or more keys, numeric, alphabetical by first tuple, etc.); Binary Large Object (BLOB); stored as ungrouped data elements encoded using ISO/IEC 7816-6 data elements; stored as ungrouped data elements encoded using ISO/IEC Abstract Syntax Notation (ASN.1) as in ISO/IEC 8824 and 8825; and/or other proprietary techniques that may include fractal compression methods, image compression methods, etc.

In various embodiments, the ability to store a wide variety of information in different formats is facilitated by storing the information as a BLOB. Thus, any binary information can be stored in a storage space associated with a data set. As discussed above, the binary information may be stored in association with the system or external to but affiliated with system. The BLOB method may store data sets as ungrouped data elements formatted as a block of binary via a fixed memory offset using either fixed storage allocation, circular queue techniques, or best practices with respect to memory management (e.g., paged memory, least recently used, etc.). By using BLOB methods, the ability to store various data sets that have different formats facilitates the storage of data, in the database or associated with the system, by multiple and unrelated owners of the data sets. For example, a first data set which may be stored may be provided by a first party, a second data set which may be stored may be provided by an unrelated second party, and yet a third data set which may be stored, may be provided by an third party unrelated to the first and second party. Each of these three exemplary data sets may contain different information that is stored using different data storage formats and/or techniques. Further, each data set may contain subsets of data that also may be distinct from other subsets.

As stated above, in various embodiments, the data can be stored without regard to a common format. However, the data set (e.g., BLOB) may be annotated in a standard manner when provided for manipulating the data in the database or system. The annotation may comprise a short header, trailer, or other appropriate indicator related to each data set that is configured to convey information useful in managing the various data sets. For example, the annotation may be called a "condition header", "header", "trailer", or "status", herein, and may comprise an indication of the status of the data set or may include an identifier correlated to a specific issuer or owner of the data. In one example, the first three bytes of each data set BLOB may be configured or configurable to indicate the status of that particular data set; e.g., LOADED, INITIALIZED, READY, BLOCKED, REMOVABLE, or DELETED. Subsequent bytes of data may be used to indicate for example, the identity of the user, healthcare entity, patient account identifier or the like. Each of these condition annotations are further discussed herein.

The data set annotation may also be used for other types of status information as well as various other purposes. For example, the data set annotation may include security information establishing access levels. The access levels may, for example, be configured to permit only certain individuals, levels of employees, companies, or other entities to access data sets, or to permit access to specific data sets based on the various entities involved. Furthermore, the security information may restrict/permit only certain actions such as accessing, modifying, and/or deleting data sets. In one example, the data set annotation indicates that only the data set owner or the user are permitted to delete a data set, various identified users may be permitted to access the data set for reading, and others are altogether excluded from accessing the data set. However, other access restriction parameters may also be used allowing various entities to access a data set with various permission levels as appropriate.

The data, including the header or trailer may be received by a standalone interaction device configured to add, delete, modify, or augment the data in accordance with the header or trailer. As such, in one embodiment, the header or trailer is not stored on a device along with the associated data, but instead the appropriate action may be taken by providing to the user at the standalone device, the appropriate option for the action to be taken. The system may contemplate a data storage arrangement wherein the header or trailer, or header or trailer history, of the data is stored on the system, device or app in relation to the appropriate data.

One skilled in the art will also appreciate that, for security reasons, any databases, systems, devices, servers or other components of the system may consist of any combination thereof at a single location or at multiple locations, wherein each database or system includes any of various suitable security features, such as firewalls, access codes, encryption, decryption, compression, decompression, and/or the like.

Encryption may be performed by way of any of the techniques now available in the art or which may become available—e.g., Twofish, RSA, El Gamal, Schorr signature, DSA, PGP, PKI, GPG (GnuPG), and symmetric and asymmetric cryptosystems.

The computing unit of the web client may be further equipped with an Internet browser connected to the Internet or an intranet using standard dial-up, cable, DSL or any other Internet protocol known in the art. Data or operations originating at a web client may pass through a firewall in order to prevent unauthorized access from users of other networks. Further, additional firewalls may be deployed between the varying components of CMS to further enhance security.

Firewall may include any hardware and/or software suitably configured to protect CMS components and/or enterprise computing resources from users of other networks. Further, a firewall may be configured to limit or restrict access to various systems and components behind the firewall for web clients connecting through a web server. Firewall may reside in varying configurations including Stateful Inspection, Proxy based, access control lists, and Packet Filtering among others. Firewall may be integrated within a web server or any other CMS components or may further reside as a separate entity. A firewall may implement network address translation ("NAT") and/or network address port translation ("NAPT"). A firewall may accommodate various tunneling protocols to facilitate secure communications, such as those used in virtual private networking. A firewall may implement a demilitarized zone ("DMZ") to facilitate communications with a public network such as the Internet. A firewall may be integrated as software within an Internet server, any other application server components or may reside within another computing device or may take the form of a standalone hardware component.

The computers discussed herein may provide a suitable website or other Internet-based graphical user interface which is accessible by users. In one embodiment, the MICROSOFT® INTERNET INFORMATION SERVICES® (IIS), MICROSOFT® Transaction Server (MTS), and MICROSOFT® SQL Server, are used in conjunction with the MICROSOFT® operating system, MICROSOFT® NT web server software, a MICROSOFT® SQL Server database system, and a MICROSOFT® Commerce Server. Additionally, components such as Access or MICROSOFT® SQL Server, ORACLE®, Sybase, Informix MySQL, Interbase, etc., may be used to provide an Active Data Object (ADO) compliant database management system. In one embodiment, the Apache web server is used in conjunction with a Linux operating system, a MySQL database, and the Perl, PHP, Ruby, and/or Python programming languages.

Any of the communications, inputs, storage, databases or displays discussed herein may be facilitated through a website having web pages. The term "web page" as it is used herein is not meant to limit the type of documents and applications that might be used to interact with the user. For example, a typical website might include, in addition to standard HTML documents, various forms, JAVA® applets, JAVASCRIPT, active server pages (ASP), common gateway interface scripts (CGI), extensible markup language (XML), dynamic HTML, cascading style sheets (CSS), AJAX (Asynchronous JAVASCRIPT And XML), helper applications, plug-ins, and the like. A server may include a web service that receives a request from a web server, the request including a URL and an IP address (123.56.789.234). The web server retrieves the appropriate web pages and sends the data or applications for the web pages to the IP address. Web services are applications that are capable of interacting with other applications over a communications means, such as the internet. Web services are typically based on standards or protocols such as XML, SOAP, AJAX, WSDL and UDDI. Web services methods are well known in the art, and are covered in many standard texts. See, e.g., ALEX NGHIEM, IT WEB SERVICES: A ROADMAP FOR THE ENTERPRISE (2003), hereby incorporated by reference. For example, representational state transfer (REST), or RESTful, web services may provide one way of enabling interoperability between applications.

Middleware may include any hardware and/or software suitably configured to facilitate communications and/or process transactions between disparate computing systems. Middleware components are commercially available and known in the art. Middleware may be implemented through commercially available hardware and/or software, through custom hardware and/or software components, or through a combination thereof. Middleware may reside in a variety of configurations and may exist as a standalone system or may be a software component residing on the Internet server. Middleware may be configured to process transactions between the various components of an application server and any number of internal or external systems for any of the purposes disclosed herein. WEBSPHERE MQ™ (formerly MQSeries) by IBM®, Inc. (Armonk, N.Y.) is an example of a commercially available middleware product. An Enterprise Service Bus ("ESB") application is another example of middleware.

Practitioners will also appreciate that there are a number of methods for displaying data within a browser-based document. Data may be represented as standard text or within a fixed list, scrollable list, drop-down list, editable text field, fixed text field, pop-up window, and the like. Likewise, there are a number of methods available for modifying data in a web page such as, for example, free text entry using a keyboard, selection of menu items, check boxes, option boxes, and the like.

The system and method may be described herein in terms of functional block components, screen shots, optional selections and various processing steps. It should be appreciated that such functional blocks may be realized by any number of hardware and/or software components configured to perform the specified functions. For example, the system may employ various integrated circuit components, e.g., memory elements, processing elements, logic elements, look-up tables, and the like, which may carry out a variety of functions under the control of one or more microprocessors or other control devices. Similarly, the software elements of the system may be implemented with any programming or scripting language such as C, C++, C#, JAVA®, JAVASCRIPT, JAVASCRIPT Object Notation (JSON), VBScript, Macromedia Cold Fusion, COBOL, MICROSOFT® Active Server Pages, assembly, PERL, PHP, awk, Python, Visual Basic, SQL Stored Procedures, PL/SQL, any UNIX shell script, and extensible markup language (XML) with the various algorithms being implemented with any combination of data structures, objects, processes, routines or other programming elements. Further, it should be noted that the system may employ any number of conventional techniques for data transmission, signaling, data processing, network control, and the like. Still further, the system could be used to detect or prevent security issues with a client-side scripting language, such as JAVASCRIPT, VBScript or the like. For a basic introduction of cryptography and network security, see any of the following references: (1) "Applied Cryptography: Protocols, Algorithms, And Source Code In C," by Bruce Schneier, published by John Wiley & Sons (second edition, 1995); (2) "JAVA® Cryptography" by Jonathan Knudson, published by O'Reilly & Associates (1998); (3) "Cryptography & Network Security: Principles & Practice" by William Stallings, published by Prentice Hall; all of which are hereby incorporated by reference.

In various embodiments, the software elements of the system may also be implemented using Node.js®. Node.js® may implement several modules to handle various core functionalities. For example, a package management module, such as Npm®, may be implemented as an open source library to aid in organizing the installation and management of third-party Node.js® programs. Node.js® may also implement a process manager, such as, for example, Parallel Multithreaded Machine ("PM2"); a resource and performance monitoring tool, such as, for example, Node Application Metrics ("appmetrics"); a library module for building user interfaces, such as for example ReachJS®; and/or any other suitable and/or desired module.

As will be appreciated by one of ordinary skill in the art, the system may be embodied as a customization of an existing system, an add-on product, a processing apparatus executing upgraded software, a stand alone system, a distributed system, a method, a data processing system, a device for data processing, and/or a computer program product. Accordingly, any portion of the system or a module may take the form of a processing apparatus executing code, an internet based embodiment, an entirely hardware embodiment, or an embodiment combining aspects of the internet, software and hardware. Furthermore, the system may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

The system and method is described herein with reference to screen shots, block diagrams and flowchart illustrations of methods, apparatus (e.g., systems), and computer program products according to various embodiments. It will be understood that each functional block of the block diagrams and the flowchart illustrations, and combinations of functional blocks in the block diagrams and flowchart illustrations, respectively, can be implemented by computer program instructions.

These computer program instructions may be loaded onto a general purpose computer, special purpose computer, or other programmable data processing apparatus to produce a machine, such that the instructions that execute on the computer or other programmable data processing apparatus create means for implementing the functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions which execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems which perform the specified functions or steps, or suitable combinations of special purpose hardware and computer instructions. Further, illustrations of the process flows and the descriptions thereof may make reference to user WINDOWS®, webpages, websites, web forms, prompts, etc. Practitioners will appreciate that the illustrated steps described herein may comprise in any number of configurations including the use of WINDOWS®, webpages, web forms, popup WINDOWS®, prompts and the like. It should be further appreciated that the multiple steps as illustrated and described may be combined into single webpages and/or WINDOWS® but have been expanded for the sake of simplicity. In other cases, steps illustrated and described as single process steps may be separated into multiple webpages and/or WINDOWS® but have been combined for simplicity.

The term "non-transitory" is to be understood to remove only propagating transitory signals per se from the claim scope and does not relinquish rights to all standard computer-readable media that are not only propagating transitory signals per se. Stated another way, the meaning of the term "non-transitory computer-readable medium" and "non-transitory computer-readable storage medium" should be construed to exclude only those types of transitory computer-readable media which were found in In Re Nuijten to fall outside the scope of patentable subject matter under 35 U.S.C. § 101.

Benefits, other advantages, and solutions to problems have been described herein with regard to specific embodiments. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to 'at least one of A, B, and C' or 'at least one of A, B, or C' is used in the claims or specification, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C.

All structural, chemical, and functional equivalents to the elements of the above-described various embodiments that are known to those of ordinary skill in the art are expressly incorporated herein by reference and are intended to be encompassed by the present claims. Moreover, it is not necessary for an apparatus or component of an apparatus, or method in using an apparatus to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims. No claim element is intended to invoke 35 U.S.C. 112(f) unless the element is expressly recited using the phrase "means for." As used herein, the terms "comprises", "comprising", or any other variation thereof, are intended to cover a non-exclusive inclusion, such that a chemical, chemical composition, process, method, article, or apparatus that comprises a list of elements does not include only those elements but may include other elements not expressly listed or inherent to such chemical, chemical composition, process, method, article, or apparatus.

We claim:

1. An infection control method comprising:
    (1) creating, by a computer-based system, an asset record for each of one or more assets within a facility;
    (2) tagging, by the computer-based system, each asset with a barcode or RFID tag associated with each asset record;
    (3) obtaining, by the computer-based system, a first location for each asset;
    (4) obtaining, by the computer-based system, a first measure of pathogen contamination for each asset;
    (5) acquiring, by the computer-based system, the first location and the first measure of pathogen contamination for each asset as a first set of data;
    (6) obtaining, by the computer-based system, a second location for each asset after passage of a prescribed length of time;
    (7) obtaining, by the computer-based system, a second measure of pathogen contamination for each asset after passage of the prescribed length of time;
    (8) acquiring, by the computer-based system, the second location and second measure of pathogen contamination for each asset as a second set of data;
    (9) analyzing, by the computer-based system, the sets of data to generate a report including a list of assets identified as critical control points; and
    (10) disposing, by the computer-based system, a residual self-sanitizing coating composition on each asset identified as a critical control point.

2. The infection control method of claim 1, further comprising repeating steps (6) through (8) to provide additional sets of data for the analyzing in step (9).

3. The infection control method of claim 1, wherein the facility comprises a healthcare or foodservice facility.

4. The infection control method of claim 1, wherein the step of (6) obtaining, by the computer-based system, a second location for each asset after passage of a prescribed length of time further comprises RFID tag inventory by a plurality of RFID readers distributed around the inside of the facility.

5. The infection control method of claim 1, wherein the prescribed length of time is 24 hours.

6. The infection control method of claim 1, wherein at least one of (4) obtaining, by the computer-based system, a first measure of pathogen contamination for each asset and (7) obtaining, by the computer-based system, a second measure of pathogen contamination for each asset after passage of the prescribed length of time further comprises swabbing a surface of an asset with an environmental test swab and counting CFUs on inoculated and incubated agar plates.

7. The infection control method of claim 1, wherein the step (9) analyzing, by the computer-based system, the sets of data to generate a report including a list of assets identified as critical control points further comprises classifying an asset as a critical control point if the asset meets a predetermined criterion.

8. The infection control method of claim 7, wherein the predetermined criterion comprises a measurable pathogen contamination on the asset in two consecutive sets of data.

9. The infection control method of claim 7, wherein the predetermined criterion comprises movement of the asset from an initial location to a new location in two consecutive sets of data and a measurable pathogen contamination in the second of the two consecutive sets of data appearing on a previously clean asset in the new location of the moved asset in the second of the two consecutive sets of data.

10. The infection control method of claim 1, wherein the step (7) obtaining, by the computer-based system, a second measure of pathogen contamination for each asset after passage of the prescribed length of time further comprises DNA or RNA sequencing of pathogens.

11. The infection control method of claim 10, wherein the DNA or RNA sequencing of pathogens is used by the computer-based system in the step (9) analyzing to determine the extent of mutations between instances of a pathogen, how long the pathogen has existed, how far it has been transferred, and if the pathogen has been physically transferred between any two assets by remaining viable on an asset that has been relocated in the facility.

12. The infection control method of claim 1, wherein the step (10) disposing, by the computer-based system, a residual self-sanitizing coating composition on each asset identified as a critical control point further comprises at least one of manual spraying, compressed air spraying, electrostatic spraying, and aerosol spraying a surface of each asset identified as a critical control point.

13. The infection control method of claim 1, wherein the residual self-sanitizing coating composition comprises 3-(trimethoxysilyl) propyl dimethyl octadecyl ammonium chloride.

14. The infection control method of claim 1, wherein the computer-based system comprises an infection control apparatus comprising: an asset tagging unit; a spraying unit; a power supply unit; and a computing unit comprising a non-transitory computer-readable medium encoded with program instructions for controlling the asset tagging unit and the spraying unit to perform the method of infection control in the facility.

15. The infection control method of claim 14, wherein the program instructions further comprise RFID asset management and tracking software programming.

* * * * *